United States Patent [19]
Wiebe et al.

[11] Patent Number: 5,739,121
[45] Date of Patent: Apr. 14, 1998

[54] FLUOROCYCLOSACCHARIDE DRUG DELIVERY SYSTEMS

[75] Inventors: Leonard I. Wiebe; James Diakur, both of Edmonton, Canada

[73] Assignee: University of Alberta, Edmonton, Canada

[21] Appl. No.: 354,777

[22] Filed: Dec. 12, 1994

[30] Foreign Application Priority Data

Dec. 10, 1993 [GB] United Kingdom ............... 9325330

[51] Int. Cl.⁶ ............... A61K 31/175; A61K 51/00; C08B 37/16
[52] U.S. Cl. ............... 514/58; 424/9.35; 536/103
[58] Field of Search ............... 536/103, 123.1; 514/54, 58; 424/9.35

[56] References Cited

U.S. PATENT DOCUMENTS 5,068,227  11/1991  Weinshenker ............... 514/58

FOREIGN PATENT DOCUMENTS 531016  3/1993  European Pat. Off. .
9112824  9/1991  WIPO .

OTHER PUBLICATIONS

Szejtli, J. "Medicinal Applications of Cyclodextrins", from *Medicinal Research Reviews*, vol. 14(3):353–386, (1994).
*Carbohydrates*, Ed. by P.M Collins, Publ. Chapman & Hall, pp. 150–151, (1987).
Wright et al., *J. Org. Chem.*, vol. 34:2632, (1969).
*Carbohydrate Research*, vol. 143: 106–117, (1985).
Naser–Hijazi, B. Hull. Locoregional Adminstration of 5–fluoro–2'–deoxyuridine (FdUrd) in Novikoff Hepatoma in the Rat: Effects of Dose and Infusion Time on Tumor Growth and on FdUrd Metabolite Levels in Tumor Tissue as Determined by $^{19}$F–NMR Spectroscopy. *J. Cancer Res. Clin. Oncol.*, 117, 295–304 (1991).
Koutcher, J.A., *In Vivo* Monitoring of Changes in 5–FluorouracilMetabolism Induced by $^{19}$F–NMR Spectroscopy. *Magnetic Resonance in Med.*, 19, 113–123 (1991).
Port, R.E., B. Bachert and W. Semmler. Kinetic Modeling of in vivo–Nuclear Magnetic Resonance Spectroscopy Data: 5–Fluorouracil in Liver and Liver Tumors. *Clin. Pharmacol. Ther.*, 49, 497–505 (1991).
McSheehy, P.M.J., M.J.W. Prior and J.R. Griffiths. Prediction of 5–Fluorouracil Cytotoxicity Towards the Walker Carcinosarcoma Using Peak Integrals of Fluoronucleotides Measured by MRS *in vivo Br. J. Cancer*, 60, 303–309 (1989).
Zhang, R., S–J Soong, T. Liu, S. Barnes and R.B. Diasio. Pharmacokinetics and Tissue Distribution of 2–Fluoro–β–alanine in Rats. Potential Relevance to Toxicity Pattern of 5–Fluorouracil. *Drug Metab. and Disp.*, 20, 113–119 (1992).

Maxwell, R.J., T.A. Frenkiel, D.R. Newell, C. Bauer and J.R. Griffiths. $^{19}$F Nuclear Magnetic Resonance Imaging of Drug Distribution *in Vivo*: The Disposition of an Antifolate Anticancer Drug in Mice. *Magnetic Resonance in Med.*, 17, 196 (1991).
Thomas, C., C. Counsell, P. Wood and G.E. Adams. Use of Fluorine–19 Nuclear Magnetic Resonance Spectroscopy and Hydralazine for Measuring Dynamic Changes in Blood Perfusion Volume in Tumors in Mice. *J.N.C.I.*, 84, 174–180 (1992).
Tandon, M., P. Kumar, G. Wiebe and L.I. Wiebe. Detection of New Metabolites of Trifluridine ($F_3$TdR) Using $^{19}$F NMR Spectroscopy. *Biochem. Pharmacol.*, 44, 2223–2228 (1992).
Tandon, M., P. Kumar and L.I. Wiebe. ∝–Trifluoromethyl–α–ureido–proprionic acid ($F_3$MUPA) : a new metabolite of trifluridine ($F_3$TdR). *Nucleosides and Nucleotides.*, 12(8) in press (1993).
Tandon, M., P. Kumar and L.I. Wiebe, ∝–Trifluoromethly–α–alanyl glycine ($F_3$MBAG): A novel metabolite of trifluorouridine ($F_3$TdR). (submitted).
Heidelberger, D., J. Boohar and B. Kampschoer. Fluorinated Pyrimidines XXIV in vivo Metabolism of 5–Trifluoromethyluracil–2–14–C and 5–Trifluoromethyl–2'–deoxyuridine–2–14–C. *Cancer Res.*, 25, 377–381 (1964).
Cramer, F. and H. Hettler. Inclusion Compounds of Cyclodextrins. *Naturwissenschaften*, 54, 624–632 (1967).
Uekama, K. Pharmaceutical Applications of Methylated Cyclodextrins. *Pharm. Int.*, Mar., 61–64 (1985); Uekema, K. and Otagiri, M. Cyclodextrins in Drug Cancer Systems. *CRC Cric. Rev. Therap. Drug Cancer Systems*, 3, 1 (1987).
Green, A.R. and J.K. Guillory. Heptakis (2,6–di–O–methyl)–β–cyclodextrin Complexation with Antitumor Agent Chlorambucil. *J. Pharm. Sci.*, 78, 427–341 (1989).
Brewster, M.E., J.W. Simpkins, M. S. Hora, W.C. Stern and N. Bodor. The Potential Use of Cyclodextrins in Parenteral Formulations. *J. Parenteral Sci. and Tech.*, 43, 231–240 (1989).
Pitha, J. et al. Hydroxypropyl–β–cyclodextrin: Preparation and Characterization; Effects on Solubility of Drugs, *Int. J. Pharm.*, 29, 73–82 (1986).

(List continued on next page.)

*Primary Examiner*—John Kignt
*Assistant Examiner*—Howard C. Lee
*Attorney, Agent, or Firm*—Nikaido Marmelstein Murray & Oram, LLP

[57] ABSTRACT

Novel fluorine-containing cyclic saccharide compounds, in particular fluorocyclodextrin compounds, and drug inclusion complexes of these compounds, as well as methods for preparation of the novel fluorine-containing cyclic saccharide compounds, including fluorocyclodextrins, and drug inclusion complexes of the compounds. In addition, methods for following the disposition and fate in vivo of drug inclusion complexes of the invention.

25 Claims, 13 Drawing Sheets

OTHER PUBLICATIONS

Szejtli, J., A. Liptak, I. Jodal, P. Fugedi, P. Nánási and A. Neszmelyi. Synthesis and $^{13}$C-NMR Spectroscopy of Methylated beta-Cyclodextrins. *Starch/Stärke* 32, 165-169 (1980).

Valsami, G.N. et al. Complexation Studies of Cyclodextrins with Tricyclic Antidepressants Using Ion-selective Electrodes. *Pharm. Res.*, 9, 94-100 (1992).

Frijlink, H.W. et al. The Pharmacokinetics of β-cyclodextrin in the Rat. *Pharm. Res.*, 7, 1248-1252 (1990).

Frijlink, H.W. et al. The Effect of Cyclodextrins on the Disposition of Intravenously-injected Drugs in the Rat. *Pharm. Res.*, 8, 380-384 (1991).

Loftsson, T. and B.J. Olafsdottir. Cyclodextrin-accelerated Degradation of β-lactain Antibiotics in Aqueous Solution. *Int. J. Pharm.*, 67, R5-7 (1991).

Irie, T., K. Fukunaga, A. Yoshida, K. Uekama, H. Fales and J. Pitha. Anorphorus Water-soluble Derivatives of Cyclodextrins: 2-Hydroxyethyl, 3-Hydroxypropyl, 2-Hydroxyisobutyl and Carboxamidomethyl Derivatives of β-cyclodextrin. *Pharm. Res.*, 5, 713-719 (1988).

Brereton, I.M., T.M. Spotswood, S.F. Lincoln and E.H. Williams. Fluorine-19 Magnetic Resonance Study of the Inclusion of Fluoro-and Difluoro-*trans*-cinnamates by α-cyclodextrin. *J. Chem. Soc., Faraday Trans.*, 1, 80, 3147-3156 (1984).

Lincoln, S.F., A.M. Hounslow, J.H. Coates and B.G. Dodderidge. The Inclusion of Difluorisal by α and β-Cyclodextrins. A $^{19}$F Nuclear Magnetic Resonance and Spectrophotometric Study. *J. Chem. Soc. Faraday Trans.*, 1, 83, 2697-2703 (1987).

Pisaniello, D.L., S.F. Lincoln and J.H. Coates. The Inclusion of Haloperidol and Trifluperidol by α- and β-cyclodextrins. *J. Chem. Soc. Faraday Trans.*, 1, 81, 1247-1253 (1985).

Smith, N.J. T.M. Spostwood and S.F. Lincoln. The Inclusion of the Enantiomers of N-Trifluoroacetyl-4-fluorophenylalanine and N-Trifluoroacetylphenylalanine by cyclomaltohexose a $^2$H and $^{19}$F-N.M.R. Study. *Carbohydr. Res.*, 192, 915 (1989).

Brown, S.E., J.H. Coates, S.F. Lincoln, D.R. Coghlan and C.J. Easton. Chiral Molecular Recognition: A $^{19}$F Nuclear Magnetic Resonance Study of the Diastereoisomer Inclusion Complexes formed between Fluorinated Amino Acid Derivative and α-Cyclodextrin in Aqueous Solution. *J. Chem. Soc. Faraday Trans.*, 1, 87, 2699-2703 (1991).

Card, P.J. Fluorinated Carbohydrates. Use of (diethylamine) sulfur trifluoride in the synthesis of fluorinated sugars. *J. Org. Chem.*, 48, 393-395 (1983).

Kumadaki, I. A review in *Yakugaku Zasshi*, 4095 (1969), cited in "Synthetic Procedures in Nucelic Acid Chemistry", vol. I, ed. by W.W. Zorbach and R.S. Tipson, Pub. Interscience Publishers (1968).

Glaudemans, C.P.J. and Fletcher, H.G. Jr. *J. Org. Chem.*, 28, 3004 (1963), cited in "Synthetic Procedures in Nucelic Acid Chemistry", vol. I, ed. by W.W. Zorbach and R.S. Tipson, Pub. Interscience Publishers (1968).

Reist, E.J., Benitez A., Goodman, L., Baker, B.R. and Lee, W.W. *J. Org. Chem.*, 27, 3274 (1962), cited in "Synthetic Procedures in Nucelic Acid Chemistry", vol. I, ed. by W.W. Zorbach and R.S. Tipson, Pub. Interscience Publishers (1968).

Reichman, U., Watanabe, K.A. and Fox, J.J. A practical synthesis of 2-deoxy-2-fluoro-D-arabinofuranose derivatives. *Carbohydr. Res.*, 42, 233-240 (1975).

Grierson, J.R., Link, J.M., Mathis, C.A., Rasey, J.S. and Krohn, K.A. A Radiosynthesis of Fluorine-18 fluoromisonidazole. *J. Nuc. Med.*, 30, (3), 343-350 (1989).

Shimada, K., Fukuda, T.T. *Japan Kokai*, 75, 46, 825 (1975) cited in "Cyclodextrins and Their Inclusion Complexes" by J. Szejtli., Publ. Akademiai Kiado, Budapest, p100 (1982).

Hoffman, J.L. and R.M. Bock. The Interaction of Cyclodextrins with Nucleic Acids. A Study of Secondary Structure in Three Transfer Ribonucleic Acids. *Biochem.*, 9, 3542-3550 (1970).

Taylor, N.F., Childs, R.F. and Brunt, R.V. Synthesis of methyl 3-deoxy-3-fluoro-β-L-xylopyranoside, Chem. Ind. 928 (1964).

Breslow, R., Czarnleckl, M.F., Amert, J. and Hamaguchi, H.J. Amer. Chem. Soc., 102, 762 (1980).

Tsujihara, K. and Kurita, H., Chem. Lett. 1333 (1978).

Cramer, F., Mackensen, G. and Sensse, K., Chem. Ber., 102, 494 (1969).

Takeo, K., Suimimoto, T. and Kuge, T., Staerke, 26, 111 (1974).

Onozuka, S., Kojima, M. Hattori, K. and Toda, F., Bull. Chem. Soc. Jpn., 53 3221 (1980).

Khan, A.R., Barton, L. and D'Souza, V.T., J. Chem. Soc., Chem. Commun. 1112-1114 (1992).

Ashton, P.R., Ellwood, P., Staton, I. and Stoddard, J.F., Angew. Chem. Int. Ed. Engl., 30, 80-81 (1991).

Gadelle, A. and Defaye, J., Angew. Chem. Int. Ed. Engl., 30, 78-79 (1991).

Wenz, Gerhard. "Cyclodextrins as Building Blocks for Supramolecular Structures and Functional Units," *Angewandie Chemie Int. Ed. Engl.* 1994. 33, 803-822.

Szejtii, "Medicinal Applications of Cyclodextrins," *Medicinal Research Reviews*, vol. 14, No. 3, 353-386 (1994).

Tetrahedron Letters No. 47, pp. 4095-4096, 1969, Pergamon Press, Printed in Great Britain.

Akira Ando et al, Faculty of Pharmaceutical Sciences, Setsunan University, Nagaotoge-cho, Hirakata, Osaka 573-01, (Japan), Synthesis of 2.2.2-Trifluoroethylated Aromatic Compounds From Aromatic Amines, p. 48.

Organic Reactions, vol. 34, Chapter 2, Fluorination by Sulfur Tetrafluoride, Chia-Lin J. Wang, pp. 319-401.

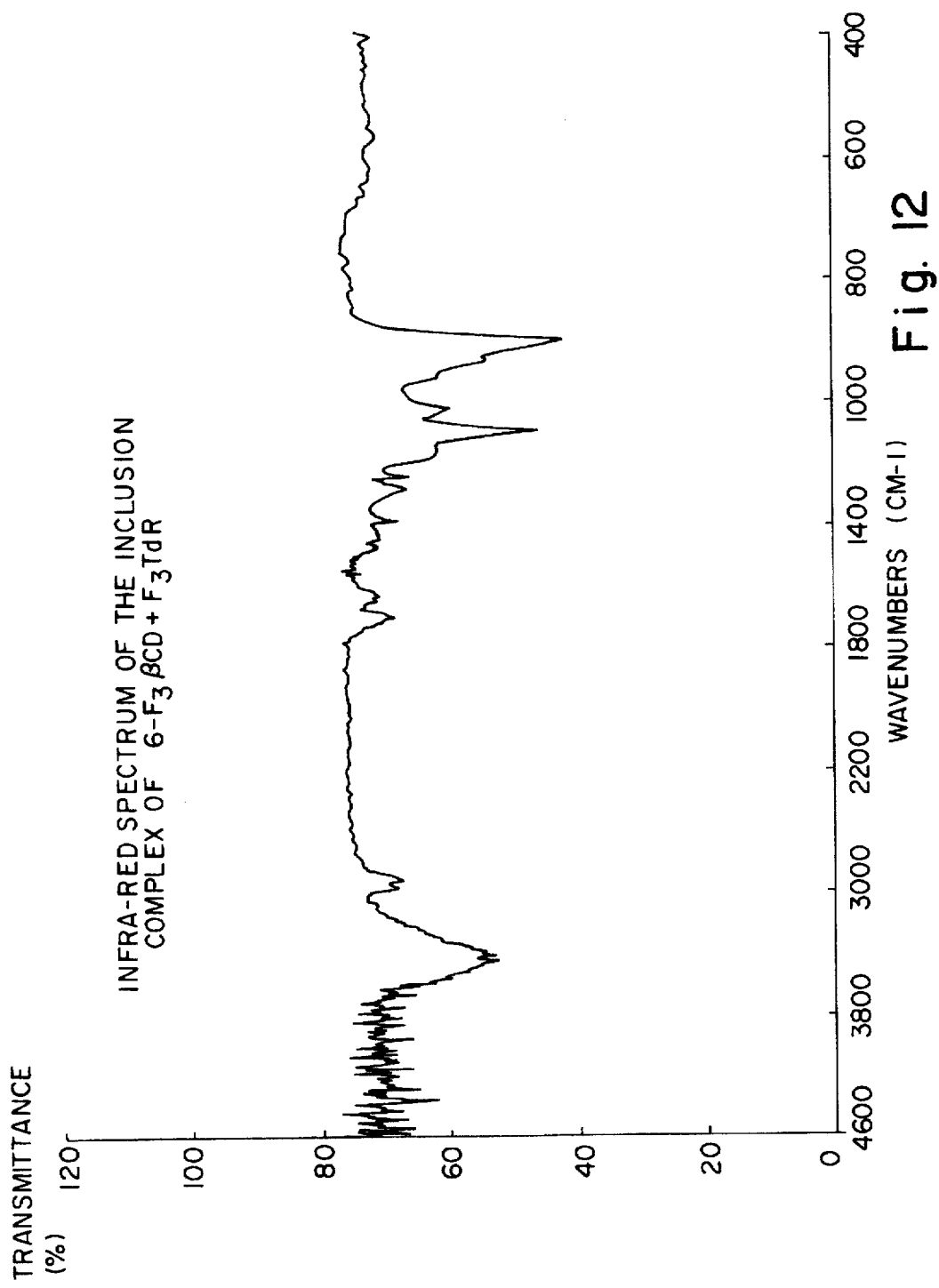

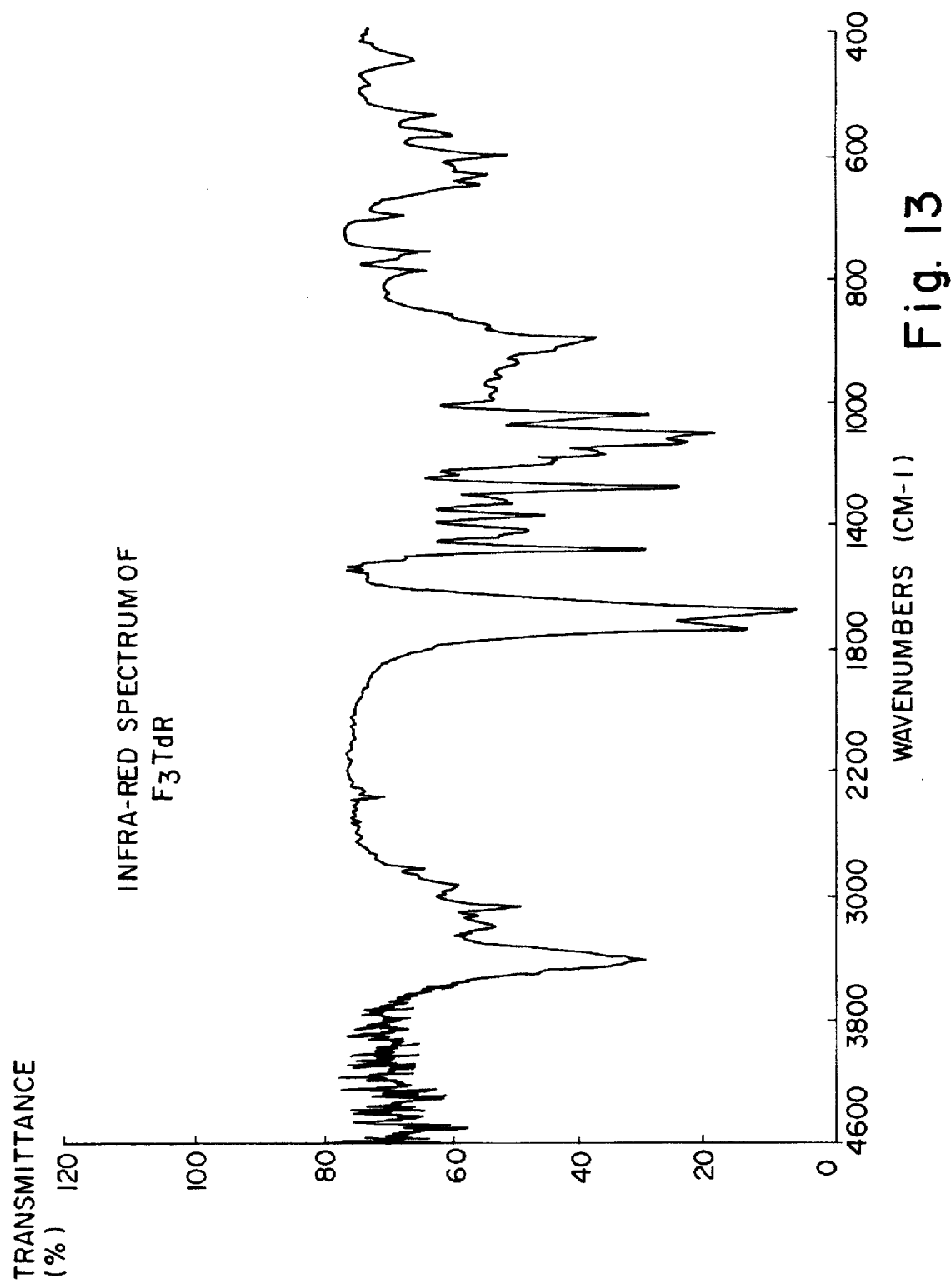

FLUOROCYCLOSACCHARIDE DRUG DELIVERY SYSTEMS

This invention relates to novel fluorine-containing cyclic saccharide compounds, in particular fluorocyclodextrin compounds, and to drug inclusion complexes of these compounds. The invention also relates to methods for preparation of the novel fluorine-containing cyclic saccharide compounds, including fluorocyclodextrins, and drug inclusion complexes of the compounds. The invention further relates to methods for following the disposition and fate in vivo of drug inclusion complexes of the invention.

BACKGROUND OF THE INVENTION

Site-specific drug delivery and trans-membrane drug delivery represent substantial challenges in the development and efficacious use of drugs. In addition, many drugs are susceptible to chemical and/or biochemical degradation on their way to their site of pharmacological action. Failure to deliver the drug for whatever reason will result in decreased efficacy. If the drug cannot reach the site of action in adequate concentrations, increased toxicity due to the requirement for larger and/or more frequent doses may seriously affect the therapeutic outcome.

BRIEF DESCRIPTION OF DRAWINGS

The invention, as exemplified by preferred embodiments, is described with reference to the accompanying drawings in which:

FIG. 12 shows IR spectrum of an inclusion complex of 6-F$_3$βCD and trifluridine.

FIG. 13 shows IR spectrum of trifluridine.

DESCRIPTION OF THE INVENTION

Figure 1:
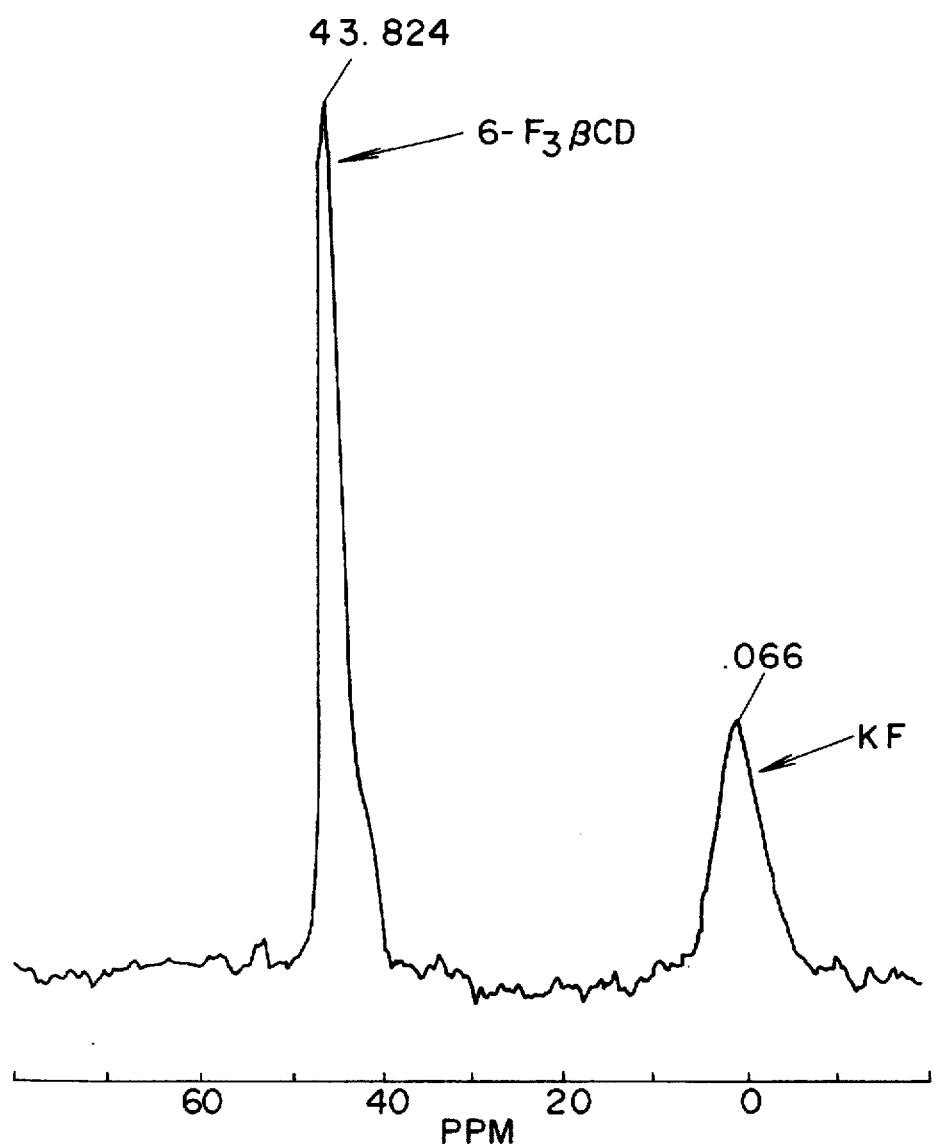
FIG. 1 shows $^{19}$F NMR spectrum of mouse liver after 6-F$_3$βCD administration.

In accordance with the present invention, a novel group of fluorine-containing cyclic saccharides are provided, including fluorocyclodextrins. These compounds permit new applicability for $^{19}$F MRS techniques in a clinically useful method.

When the compounds of the invention are used as drug carriers, there is a difference in the $^{19}$F chemical shift between the free carrier molecule and the cyclic saccharide-drug inclusion complex. This provides a novel method for determining the integrity of the complex with any drug, and is not limited to drugs which themselves contain F, as in Lincoln's system.

The change in $^{19}$F MRS chemical shift between the drug-occupied or complexed carrier and the free carrier can be used to differentiate and measure the free and complexed species. The invention provides a novel method for measuring the integrity of inclusion complexes in vivo by a method which is non-invasive and does not involve the administration of radioactive compounds to the subject.

In accordance with one aspect of the invention, methods are provided for the synthesis of fluorine-containing cyclic saccharides, including fluorocyclodextrins, and for the preparation of drug inclusion complexes employing these compounds.

A variety of cyclic saccharides are known which can form inclusion complexes with a range of chemicals/drugs/biochemicals. One type of cyclic saccharides are cyclodextrins (reference 12—the references referred to herein are listed in pages 31–36) (reference 45) (reference 46).

β-Cyclodextrin (β-CD)

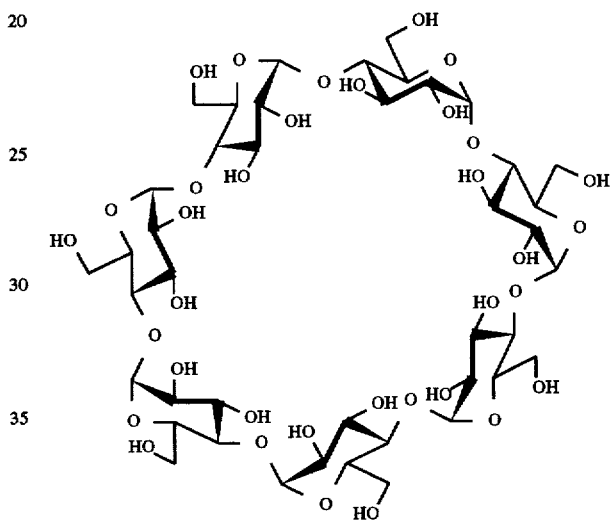

has seven 1,4-linked glycopyranose sub-units that form a toroida "basket" with an inner cavity diameter of approximately 5–7 Å. The primary hydroxyls (at C-6) are at the narrow end of the torus and the secondary hydroxyls (C-2 and C-3) are at the mouth (wide end), with the OH groups at C-2 pointing toward the cavity, while the OH groups at C-3 point outward. Thus, the outer surface becomes distinctly hydrophilic. The inner "basket" is hydrophobic, with a structure of carbon atoms and ether-oxygen atoms; this inner structure supports drug inclusion complex formation, in part through non-specific interactions (e.g. Van der Weals forces) between the drug and cyclodextrin (reference 13).

α-cyclodextrin (α-CD) is similar to β-CD, except that α-CD has only 6 sub-units. γ-cyclodextrin (γ-CD) has 8 sub-units and δ-cyclodextrin (δ-CD) has 9 sub-units (see Endo et al, "Purification and Characterization of η-Cyclodextrin," *The 7th International Cyclodextrins Symposium,* Tokyo (Apr. 25–28, 1994). Although β-CD has an ideal cavity size for the inclusion of a variety of drugs, it has two disadvantages: 1) it is nephrotoxic and 2) it has lower water solubility than either α-CD or γ-CD. It has been shown that derivatization of the primary and/or secondary hydroxyl groups can both increase its solubility and decrease its irritant properties (references 13–15).

When drugs and cyclodextrins form inclusion complexes, H-bonding and non-specific forces change in both drug and carrier molecules, giving rise to changes in the chemical shifts of nuclear magnetic resonances; if either or both molecules have fluorine in their structures, this gives rise to changes in $^{19}$F Magnetic Resonance Spectroscopy (MRS) chemical shifts.

Several fluorine-containing drugs, including flurbiprofen, have been successfully incorporated into β-CD and derivatized β-CD's as inclusion complexes (reference 13). Lincoln et al. have used $^{19}$F MRS to study the incorporation of model fluorine-containing drugs and biochemicals into cyclodextrin inclusion complexes (references 23–27); they have found $^{19}$F MRS to a useful technique to study chiral molecular recognition (references 26,17), stability/dissociation constants and drug-cyclodextrin stoichiometry in inclusion complexes, and cis/trans geometric effects (reference 23) in inclusion complexes. Their studies demonstrated and indeed were based on inclusion-complex-induced changes in the $^{19}$F MRS chemical shifts of fluorine atoms on the fluorine-containing drug. These changes are due to changes in H-bonding and to non-specific forces experienced by the drug upon inclusion complex formation.

$^{19}$F NMR or Magnetic Resonance Spectroscopy (MRS) spectroscopy is a powerful tool for the study of cyclodextrin-drug complexes, having the advantages of high sensitivity and simple spectra. To date, however, these studies have been limited to complexes involving F-containing drugs.

Other cyclic saccharides can be used, e.g., cyclic saccharides with sugars other than glucose.

The present invention is exemplified with reference to fluorine-containing cyclodextrin compounds, but the invention broadly relates to any fluorine-containing cyclic saccharide compound. The fluorine atoms can be attached to cyclic saccharides in a manner analogous to the mechanisms for attachment disclosed herein for cyclodextrin compounds and by other means, which are known by those skilled in the art and which can be practiced without any undue experimentation. Such fluorine-containing cyclic saccharide compounds will exhibit properties which are similar to the properties exhibited by the fluorine-containing compounds disclosed herein.

For example, suitable cyclic saccharides include cycloisomaltooligosaccharides (CI-7, CI-8 and CI-9, below) disclosed in Oguma et al, "Novel Cyclic Sugars, Cycloisomaltooligosaccharides, and Cycloisomaltooligosaccharide Synthase," *The 7th International Cyclodextrins Symposium*, Tokyo (Apr. 25–28, 1994).

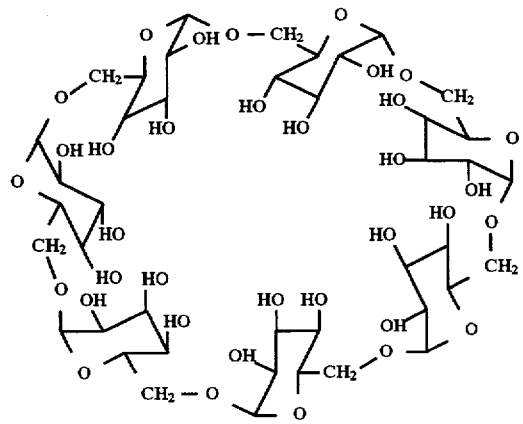

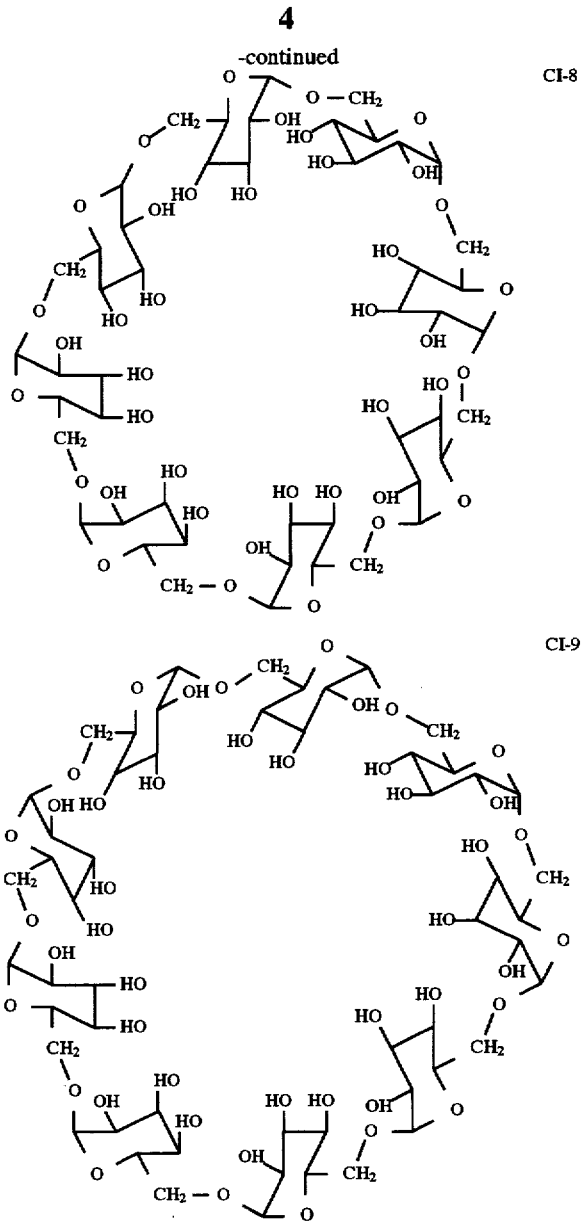

Likewise, suitable cyclic saccharides also include Maltosyl cyclodextrins as disclosed in Mikuni et al, "Continuous Production of Maltosyl Cyclodextrins Using Immobilized Pullulanase on Novel Ceramic Carrier," *The 7th International Cyclodextrins Symposium*, Tokyo (Apr. 25–28, 1994). Such Maltosyl cyclodextrins are synthesized by enzyme reaction of pullulanase from maltose and cyclodextrings such as α-CD, β-CD and γ-CD.

In addition, trimaltosyl-β-CD's disclosed in Okada et al, "Structural Determination of Positional Isomers of Multi-Branched Cyclomalto-Oligosaccharides (Cyclodextrins) by Enzymatic Degradation," *The 7th International Cyclodextrins Symposium*, Tokyo (Apr. 25–28, 1994) can be used as the cyclic saccharide according to the present invention.

The cyclodextrins of the invention can also be in the form of a molecular tube as disclosed in Li et al, "Synthesis of Tubular Polymers of Cyclodextrins by Using a Polymer Chain as Matrix," *The 7th International Cyclodextrins Symposium*, Tokyo (Apr.25–28, 1994).

Preferred cyclic saccharides according to the present invention are β-cyclodextrins.

The fluorination achieved in the fluoro-cyclic saccharides of the invention provides a signal, suitable for location of the carrier in a whole animal or in a patient, so that the location of drug delivery can be determined in vivo, using known Magnetic Resonance Imaging (MRI) techniques. By using known MRS techniques, one can follow the breakdown of the drug inclusion complexes containing the cyclic saccharides of the invention either in tissue samples taken from a subject or in whole body studies on a subject and thereby determine the rate of drug delivery and drug release to the body or its tissues.

The techniques of whole body, in vivo, in situ MRI have become routine in medical diagnosis of biochemical and anatomical lesions, and in studies of bioenergetics and xenobiotic transformations. Although MRS and MRI are applied primarily to proton ($^1$H) studies, the virtual absence of any fluorine in mammalian soft tissue and the high sensitivity of $^{19}$F (second only to $^1$H) make $^{19}$F MRS and $^{19}$F MRI unique and powerful tools for the investigation of biotransformation, biodistribution and excretion of fluorinated substances.

The advantages with $^{19}$F NMR spectra are that they are clean (few overlapping signals), easily recognizable by F—H coupling, relatively easy to interpret and not masked by a huge water signal, which is a characteristic of in vivo proton MRS.

Table 2 demonstrates the change in $^{19}$F chemical shift between compounds of the invention in their free state and in drug inclusion complex form. The inclusion complex of trifluridine and 6-F$_3$βCD appears to show no change in $^{19}$F chemical shift in comparison to the parent compound, i.e., trifluridine and 6-F$^3$βCD. It is believed that this is because trifluridine and related nucleosides are too small to achieve a considerable interaction in the cavity of β-CD (Hoffman et al., (1970), Biochem., V. 9, p. 3542) and therefore, on dilution with the NMR solvent, D$_2$O, the drug readily dissociates and the complex is lost.

Table 2 shows significant changes in the $^{19}$F chemical shift for flutamide/6-F$_3$βCD inclusion complex and flurbiprofen/6-F$_3$βCD inclusion complex.

The invention provides a method for determining in tissue samples or in a patient whether administered drug inclusion complex remains intact or has broken down to deliver free drug by examination of the $^{19}$F chemical shift in the signal obtained from the tissue or from the patient.

In order to prepare the fluorine-containing cyclic saccharide according to the present invention, a cyclic saccharide is reacted with a fluorine-containing compound. The fluorine-containing compound can generally be any compound which is suitable for either adding a fluorine atom to the cyclic saccharide or adding a moiety which contains a fluorine atom to the cyclic saccharide. This reaction can generally be conducted at any temperature from about room temperature up to about 100° C.

The following are representations of suitable processes for making fluorine-containing cyclic saccharides according to the present invention:

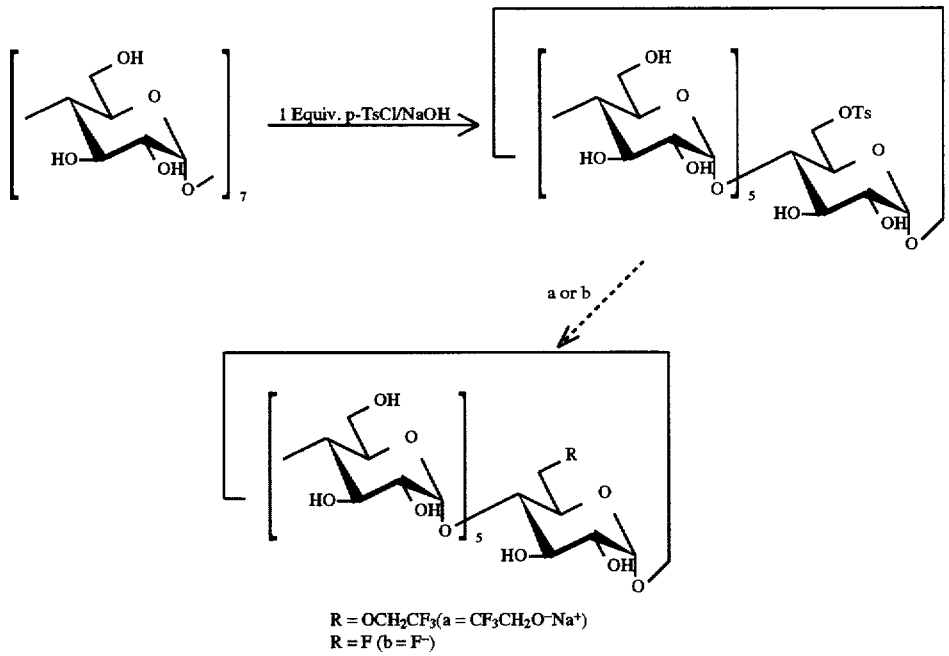

Synthesis of 6-Fluoro-β-CD
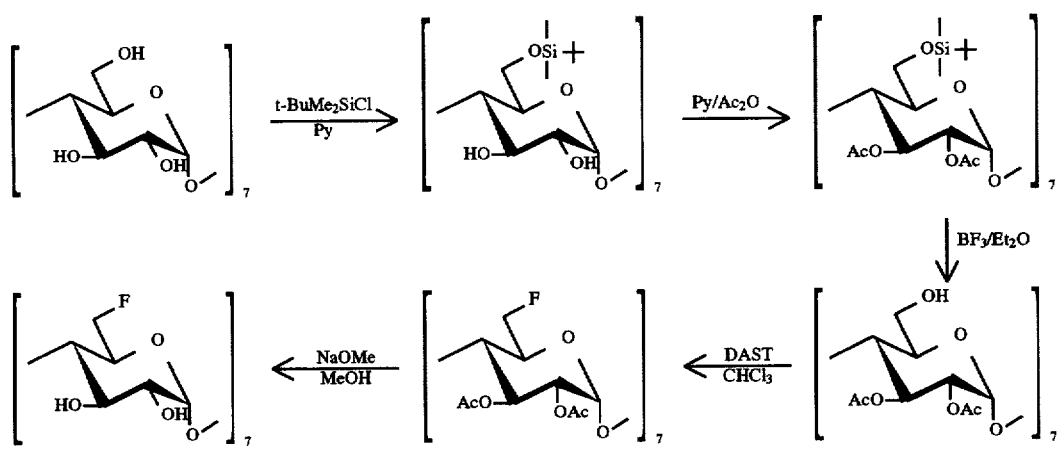
Synthesis of 3-Fluoro-β-CD
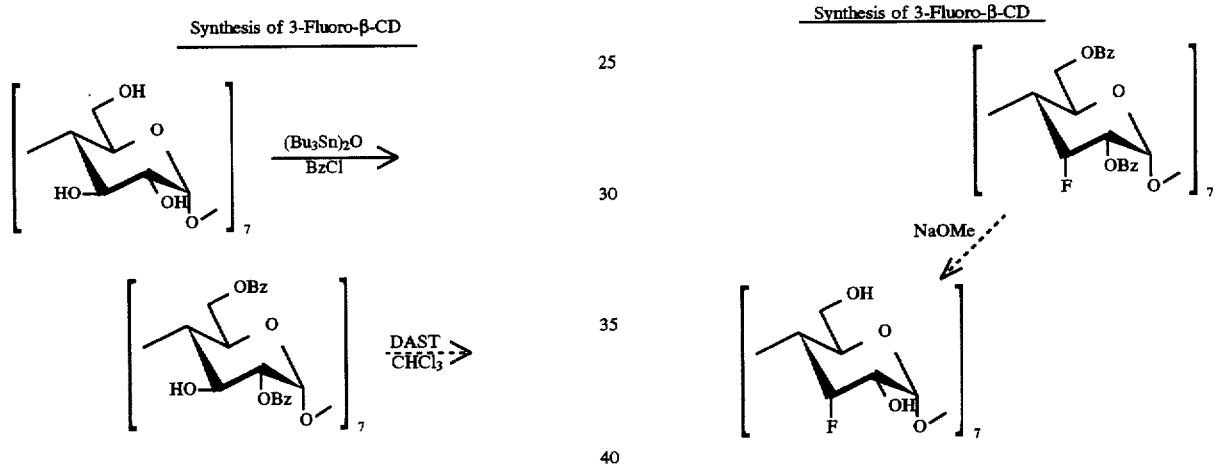
-continued
Synthesis of 3-Fluoro-β-CD
Synthesis of 3-Fluoro-Manno-β-CD
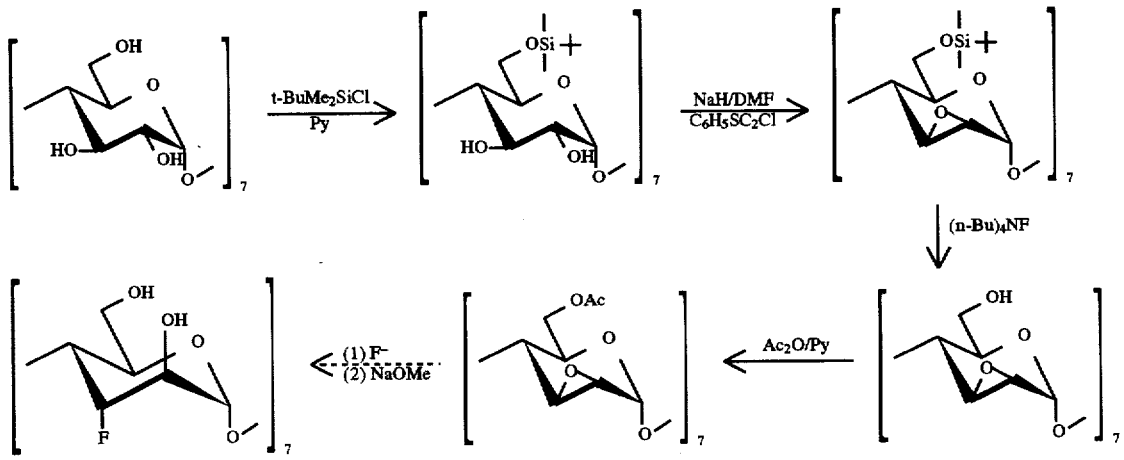

As described above, the present invention broadly relates to fluorine-containing cyclic saccharide compounds, any of which can readily be tested for its usefulness in providing the properties described herein by employing routine experimentation.

The following are representative examples of compounds in accordance with the present invention:

(i) Fluorine Substituent at the Primary Carbon Center

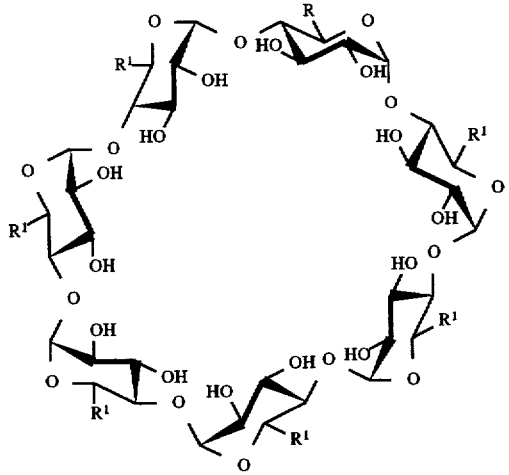

wherein:

1. $R=R^1=F$.

2. $R=CH_2F$, one or more $R^1=CH_2OH$, the remaining $R^1=CH_2F$; i.e. for β-CD, $R^1=x$ $CH_2OH$, (6–x) $CH_2F$, x=0–6.

3. $R=CH_2F$, one or more $R^1=CO_2H$, the remaining $R^1=CH_2F$; i.e. for β-CD, $R^1=x$ $CO_2H$, (6–x) $CH_2F$, x=0–6.

4. $R=CH_2F$, one or more $R^1=CH_2R^2$ (where $R^2=NH_2$ or $N_3$), the remaining $R^1=CH_2F$; i.e. for β-CD, $R^1=-x$ $CH_2R^2$ (where $R^2=NH_2$ or $N_3$), (6–x) $CH_2F$, x=0–6.

5. $R=CH_2F$, one or more $R^1=CH_2OR^2$ (where $R^2$=sugar moiety i.e. Glc, GlcNAc, Gal, GalNAc, Fuc, Neu5Ac, or other suitable sugar moieties), the remaining $R^1=CH_2F$; i.e. for β-CD, $R^1=x$ $CH_2OR^2$ (where $R^2$=sugar moiety i.e. Glc, GlcNAc, Gal, GalNAc, Fuc, Neu5Ac, or other suitable sugar moieties), (6–x) $CH_2F$, x=0–6.

6. R is $CH_2OCH_2CF_3$, $CH_2NHC_6H_4F$, or other moieties which contain fluorine.

Also, in 2–5 above, the carboxy, amino, or carbohydrate moiety can be used to build an amino acid, peptide or carbohydrate antigen in order to realize specificity through molecular recognition (i.e., receptor, antibody-antigen complex, etc.) or for enhancing solubility or complex formation.

(ii) Fluorine Substituent at a Secondary Carbon Center

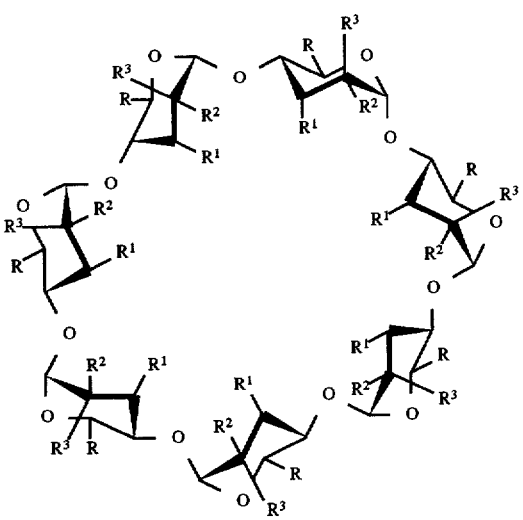

(a) Gluco Configuration

1. $R=CH_2OH$, $R^1=F$, $R^2=OH$, $R^3=H$.

2. $R^1=F$, $R^2=OH$, $R^3=H$, at least one $R=CO_2H$, the remaining $R=CH_2OH$; i.e. for β-CD, R=x $CO_2H$, (7–x) $CH_2OH$, x=0–7.

3. $R^1=F$, $R^2=OH$, $R^3=H$, at least one $R=CH_2R^4$ (where $R^4=NH_2$ or $N_3$), the remaining $R=CH_2OH$, i.e. for β-CD, R=-x $CH_2R^4$ (where $R^4=NH_2$ or $N_3$), (7–x) $CH_2OH$, x=0–7.

4. $R^1=F$, $R^2=OH$, $R^3=H$, at least one $R=CH_2R^5$ (where $R^5$=sugar moiety i. e. Glc, GlcNAc, Gal, GalNAc, Fuc, Neu5Ac, or other suitable sugar moieties), the remaining $R=CH_2OH$; i.e. for β-CD, R=x $CH_2R^5$ (where $R^5$=sugar moiety i.e. Glc, GlcNAc, Gal, GalNAc, Fuc, Neu5Ac, or other suitable sugar moieties), (7–x) $CH_2OH$, x=0–7.

Also, in 2–4 above, the carboxy, amino, or carbohydrate moiety can be used to build an amino acid, peptide or carbohydrate antigen in order to realize specificity through molecular recognition (i.e., receptor, antibody-antigen complex, etc.) or for enhancing solubility or complex formation.

(b) Manno Configuration

1. $R=CH_2OH$, $R^1=F$, $R^2=H$, $R^3=OH$.

2. $R^1=F$, $R^2=H$, $R^3=OH$, at least one $R=CO_2H$, the remaining $R=CH_2OH$; i.e. for β-CD, R=x $CO_2H$, (7–x) $CH_2OH$, x=0–7.

3. $R^1=F$, $R^2=H$, $R^3=OH$, at least one $R=CH_2R^4$ (where $R^4=NH_2$ or $N_3$), the remaining $R=CH_2OH$; i.e. for β-CD, R=x $CH_2R^4$ where $R^4=NH_2$ or $N_3$), (7–x) $CH_2OH$, x=0–7.

4. $R^1=F$, $R^2=H$, $R^3=OH$, at least one $R=CH_2OR^5$ (where $R^5$=sugar moiety i.e. Glc, GlcNAc, Gal, GalNAc, Fuc, Neu5Ac, or other suitable sugar moieties), the remaining $R=CH_2OH$; i.e. for β-CD, R=x $CH_2OR^5$ (where $R^5$=sugar moiety i.e. Glc, GlcNAc, Gal, GalNAc, Fuc, Neu5Ac, or other suitable sugar moieties), (7–x) $CH_2OH$, x=0–7.

Also, in 2–4 above, the carboxy, amino, or carbohydrate moiety can be used to build an amino acid, peptide or carbohydrate antigen in order to realize specificity through molecular recognition (i.e., receptor, antibody-antigen complex, etc.) or for enhancing solubility or complex formation.

(iii) Fluorine Substituent at a Single Secondary Carbon Center

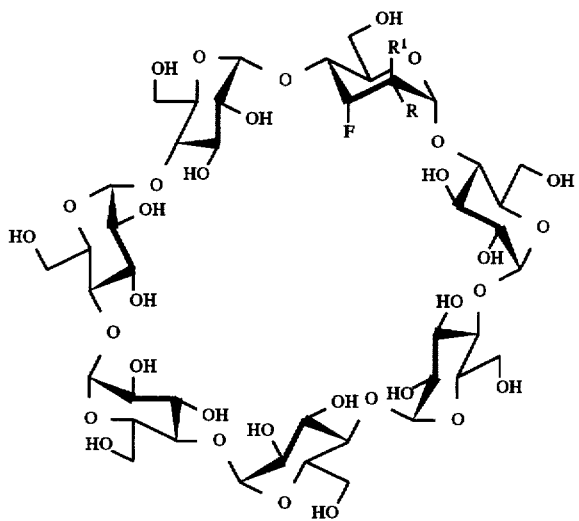

(a) Gluco Configuration
  1. R=OH, R¹=H.
(b) Manno Configuration
  1. R=H, R¹=OH.

The desired number of fluorine atoms in the fluorine-containing cyclic saccharide molecule depends on the drug being incorporated and the purpose for which the complex is being used. When the drug contains no fluorine atoms, it is generally desirable to include the maximum number of effective fluorine atoms. For example, a fluorine-containing cyclic saccharide molecule could include 21 fluorine atoms, which would provide a very large signal from the fluorine-containing cyclic saccharide when conducting $^{19}$F analysis. In instances where the drug contains one or more fluorine atom, it is desirable to provide a 1:1 ratio, i.e., the total number of fluorine atoms in the drug molecule(s) in a complex is equal to the total number of fluorine atoms in the cyclic saccharide molecule in the complex. With such a formulation, equal signals are received from the drug and from the cyclic saccharide, providing clearer signals for analyzing the drug and the cyclic saccharide both before and after release of the drug from the cyclic saccharide. If the cyclic saccharide contains more fluorine atoms than the drug in the complex, a correspondingly stronger signal is received for the cyclic saccharide, and there is a corresponding decrease in sensitivity with respect to the fate of the drug. It is preferred that the one or more fluorine atoms per molecule of cyclic saccharide be symmetrically positioned.

In accordance with the present invention, the fluorine-containing cyclic saccharide is then mixed with one or more equivalents of drug to form the inclusion complex. This step can be conducted at room temperature and/or the temperature can be elevated to accelerate the formation of the complex. As discussed above, the present invention is widely applicable to many different types of drugs, and each can be readily tested for its usefulness according to the present invention by routine experimentation.

Examples of suitable drugs for inclusion in accordance with the present invention include mitoxantrone (Novantrone)®, taxol, progesterone, testosterone, ibuprofen, hydrocortisone, digitoxin, digoxin, diazepam, and peptides. The drugs may also be fluorinated (i.e. as a second marker or for NOE experiments, e.g., fluorinated analogs of mitoxantrone, taxol, progesterone, testosterone, ibuprofen, hydrocortisone, digitoxin, digoxin, diazepam, and peptides), fluorinated amino acids and peptides, $F_3$ TDR, fluorouracil and fluorinated pyridoxyl analogs.

The ratio of fluorine-containing cyclic saccharide to the drug is typically 1:1 (on a molar basis), however, there may be instances where more than one drug molecule can be complexed by a single cyclic saccharide. Thus, the preferred ratio can readily be determined experimentally for each combination of fluorine-containing cyclic saccharide and drug.

Doses are determined in accordance with established medical techniques by routine experimentation.

The present invention also relates to pharmaceutical formulation and methods of making the same, comprising one or more inclusion complex according to the invention together with a suitable complex carrier or excipient. The selection of a complex carrier and/or excipient and the formation of pharmaceutical formulations can be carried out in accordance with well-known procedures.

The pharmaceutical compensation according to the present invention, which include a drug and a fluorine-containing cyclic saccharide according to the present invention, are suitable for treating disease states.

The inclusion complexes according to the present invention can be administered by any suitable route of administration. Such routes of administration include all of the routes well known in the art, such as, oral, parenteral, transdermal, nasal, rectal, e.g., as tablets, capsules, injectable solutions, eye-drops, etc.

The fluorine-containing cyclic saccharides in accordance with the present invention can be employed in any procedure in which the corresponding non-fluorine-containing cyclic saccharides can be employed. For example, the fluorine-containing cyclodextrins according to the present invention can be used in any circumstance in which cyclodextrins can be employed.

The present invention further relates to a process for providing site specific delivery of a drug to a patient, comprising administering to a patient a complex as disclosed herein.

The present invention further relates to a process for analyzing in vivo the location and time of drug association from a complex according to the present invention by performing $^{19}$F MRS on a patient to whom such a complex has been administered.

The present invention further relates to a process for analyzing in vivo the activity of a drug, the process comprising administering to a patient a complex as disclosed herein and performing $^{19}$F MRS on the patient.

The present invention also relates to a process for determining the location of a tumor in a patient by administering a complex as disclosed herein to the patient and performing $^{19}$F MRS on the patient.

The present invention provides a process for treating tissue extracted from a living being, comprising administering to the tissue a complex as disclosed therein.

EXAMPLES

Compounds were characterized by elemental analysis and by $^1$H, $^{13}$C and $^{19}$F NMR spectroscopy.

NMR Spectroscopy

A Bruker AM-300 (7.05 Tesla, 282.39 Mhz) and a Bruker CXP-100 (2.35 Telsa, 94.26 Mhz, 40 cm. bore) spectrometer were used for $^{19}$F NMR spectroscopy. The CXP-100 spectrometer was used with a 20 mm diameter, three turn horizontal coil. The biodistribution and excretion study of Example 4 was performed on the CXP-100 spectrometer, while $^1$H, $^{13}$C and $^{19}$F NMR spectra for synthesized compounds, blood, urine and extracts of liver were obtained using the Bruker AM-300 instrument. The $^{19}$F NMR were acquired over a spectral width of 70.0 ppm (between +60.0 and −10.0 ppm). The number of scans varied from 2.5 k to 45 k scans depending on the size of biological samples. An aqueous solution of chromium acetate (90 μL; 0.1M) was used as a relaxation agent to enhance the S/N ratio. Exponential line broadening of 0–40 Hz was imposed on the data prior to Fourier transformation. An aqueous solution of potassium fluoride (5 μL; 0.2M) was used as an internal standard during acquisition of $^{19}$F NMR spectra while $^1$H and $^{13}$C NMR spectra were locked on deuterium. $D_2O$ was used as a solvent for samples of blood, urine and liver extract) which appeared at δ4.68 ppm ($^1$H NMR spectra) with respect to tetramethylsilane. The resolution limits for $^1$H, $^{13}$C and $^{19}$F were observed between 0.5–1.1, 2.0–3.0 and 1.3–20.0 Hz, respectively. The chemical shifts are reported in δ ppm.

Example 1

Synthesis of Fluorinated Cyclodextrins

A. Anhydrous β-cyclodextrin (βCD; 4.0 g) dried overnight over refluxing methanol in a hi-vac system was dissolved in anhydrous 2,2,2-trifluoroethanol, that had been presaturated with HCl gas; the mixture was heated at 70° C. for 24 h. A TLC examination of the mixture at this time showed the formation of two major products and complete disappearance of β-CD. Usual workup and purification of this mixture on a silica gel column yielded two products:
1. Heptakis [6.0-(2,2,2-trifluoroethyl)]-β-cyclodextrin (6-F$_3$βCD)

Yield, 35.5%, mp. 122°–124° C.; $^1$H NMR (D$_2$O) δ4.94 (d, J$_{7,1}$=3.5 H$_2$, 1H, H-1), 4.18–3.94 (m, 2H, CH$_2$CF$_3$), 3.76 (d, J gem=12.0 Hz of d, J$_{5,6}$=2.0 Hz, 1H of H-6), 3.72–3.56 (m, 3H, H-5, H-6 and H-3), 3.49 (d, J$_{1,2}$=3.5 Hz of d, J$_{3,2}$=9.5 H$_2$, 1H, H-2) and 3.32 (dd, J$_{5,4}$=J$_{3,4}$=9.5 H$_2$, 1H, H-4) ppm; $^{19}$F NMR (D$_2$O+CF$_3$COOH)−δ1.60 (t, J$_{H,F}$=8.9 Hz, CF$_3$); $^{13}$C NMR (D$_2$O) δ124.56 (q, J$_{F,C}$=277.2 Hz, CF$_3$), 99.56 (C-1), 73.36 (C-3), 72.96 (C-5), 71.75 (C-2), 70.00 (C-4), 65.08 (q, J$_{F,C}$=34.9 Hz, CH$_2$CF$_3$) ppm; anal calcd. for C$_{56}$H$_{77}$O$_{42}$F$_{21}$ 9½ H$_2$O (1880.2); C, 35.70; H, 5.14; found; C, 35.67; H, 4.85%

B. Because of limited steric access and the need to maintain free 1° and 2° hydroxyls at C-6 and C-2 respectively, a modification of the synthetic process is required for heptakis (3-fluoro-3-deoxy)-β-cyclodexrin (3-FβCD). Two alternate synthetic processes follow.
1. Direct fluorination of 3-OH Group This involves replacement of free-OH group at C-3 of β-CD using strong fluorinating reagents such as diethylaminosulfur trifluoride (DAST) (reference 28) or antimony pentafluoride (SbF$_5$) (reference 29). Anhydrous 2,6-disubstituted β-CD is dissolved in an optimum quantity of anhydrous aprotic solvent and this solution is added to a precooled solution of DAST or SbF$_5$. The progress of the reaction is monitored on analytical TLC plates. This 2,6-disubstituted-3-F-intermediate, obtained after usual purification procedures is subjected to deprotection (reference 30) to obtain 3-FβCD.
2. Replacement of a Protective Group This technique involves the synthesis of 2,6-disubstituted-3-O-methane sulfonyl (or trifluoromethane-sulfonyl)-β-CD, followed by its replacement with fluoride ion. 2,6-Disubstituted-3-O-methane sulfonyl (trifluoromethane sulfonyl)-β-CD is reacted with fluoride to yield 2,6-Disubstituted-3-fluoro-β-CD which on deprotection yields the desired 3-fluoro-β-cyclodextrin (3-FβCD).

Example 2

6-F$_3$βCD/Trifluridine Inclusion Complex

This inclusion complex was prepared by a modification of the kneading method of Shimada et al. (reference 34). Trifluridine or trifluoromethyl-2'-deoxyuridine is an antiviral nucleoside.

Equimolar amounts of trifluridine (8.65 mg) and 6-F$_3$βCD (50 mg) were kneaded in a mechanical ball mill, together with a small amount of water. After 10 minutes, the resulting paste was diluted with 5 volumes of water, filtered through a 0.45μ Millipore filter and then lyophilized (reference 34). The resulting residue was very hydroscopic and required storage in a dry chamber.

Formation of the complex was confirmed by Differential Scanning Calorimetry (DSC) analysis. DSC was performed on the inclusion complex on an aluminum pad with lid, using a chamber gas purge (N$_2$; 20 Ml min$^1$); the temperature was raised at a rate of 5° C. min$^{-1}$. Trifluridine, 6-F$_3$βCD and a physical mixture (not a complex) of the two were analyzed as well, using identical conditions. DCS data are shown in Table 1 and confirm the formation of an inclusion complex.

In addition, infrared spectra were recorded for three of the materials, trifluridine, 6-F$_3$βCD and their inclusion complex, and $^{19}$F MRS studies were performed. The IR Spectra are shown in FIGS. 10 to 13. The results of the $^{19}$F MRS studies are shown in Table 2.

As will be understood by those skilled in the art, this procedure may be employed to form inclusion complexes of 6-F$_3$βCD with a variety of drugs, including trifluridine, flurbiprofen and flutamide.

TABLE 1

DSC data for 6-F$_3$β-CD, trifluridine and the 6-F$_3$β-CD/trifluridine inclusion complex

| COMPOUND | m m m H (J/g) | Temperature °C. |
|---|---|---|
| 6-F$_3$βCD | 81.92 | 123.32 |
| trifluridine | −105.30 | 190.90 |
|  | +50.55 | 203.60 |
| inclusion | +30.21 | 60.58 |
|  | −39.53 | 87.71 |
|  | −17.19 | 131.04 |

TABLE 2

$^{19}$F NMR Chemical Shifts of 6-F$_3$β-CD and their inclusion Complexes

| COMPOUND | $^{19}$F NMR | DEUTERATED SOLVENT |
|---|---|---|
| 6-F$_3$βCD | 2.07 (triplet) | CD$_3$OD (FIG. 1) |
| Trifluoridine (F$_3$TdR) | 12.17 (singlet) | D$_2$O |
| inclusion complex of F$_3$TdR with 6-F$_3$βCD | F$_3$TdR 12.17 (singlet) 6-F$_3$βCD 1.60 (triplet) | D$_2$O |
| Flutamide | 15.86 (singlet) | CD$_3$OD (FIG. 2) |
| inclusion complex of Flutamide with 6-F$_3$βCD | Flutamide 15.79 (singlet) 6-F$_3$βCD 2.05 (triplet) | CD$_3$OD (FIG. 3) |

TABLE 2-continued

$^{19}$F NMR Chemical Shifts of 6-F$_3$β-CD and their inclusion Complexes

| COMPOUND | $^{19}$F NMR | DEUTERATED SOLVENT |
|---|---|---|
| Flurbiprotein inclusion complex of Flurbiprotein 6-F$_3$βCD | –42.53 (triplet) Fluribiprotein –42.61 (triplet) 6-F$_3$βCD 2.05 (triplet) | CD$_3$OD (FIG. 4) CD$_3$OD (FIG. 5) |

All the chemical shifts are in comparison with sodium trifluoroacetic acid (TFA) used as internal standard.

As will be understood by those skilled in the art, the same process may be employed to prepare inclusion complexes of 3-FβCD.

Example 3

Synthesis of Heptakis (6-Fluoro-6-Deoxy)-β-Cyclodextrin (6-FβCD)

A.1. Direct fluorination of 6-OH group

This involves reaction of free OH group using strong fluorinating agents such as diethylaminosulfur trifluoride (DAST) (reference 28), antimony pentafluoride (SbF$_5$) (reference 29) or hydrogen fluoride (reference 36). In a typical reaction, β-CD is taken in an appropriate solvent and treated with the fluorinating agent in an appropriate reaction vessel. The reaction conditions vary with the nature of fluorinating reagent. The crude reaction mixture is subjected to column chromatography to obtain the pure product.

A.2. Replacement of a protective/halo group at C-6

This involves the substitution of heptakis 6-O-alkyl/aryl sulfonyl β-CD (references 37,38) or of a heptakis (6-halo-6-deoxy)-β-CD (references 39,40) with a) metal fluorides (AgF, AgF$_2$, KF etc.) or b) DAST or c) HF/dioxane.

B. Synthesis of heptakis (3-fluoro-3-deoxy)-β-cyclodextrin (3-FβCD) and heptakis (2-fluoro-2-deoxy)-β-cyclodextrin (2-FβCD)

B.1. Replacement of a protective group

This involves substitution of a protective group at C-3 (to obtain 3-Fβ-CD) (reference 41) with a proper fluorinating agent as described in section A.1.

B.2. Opening of an epoxy linkage between C-2 and C-3 of β-CD

This involves the reaction of heptakis (2,3-epoxy)-βcyclodextrin (reference 42) with a desired fluorinating agent. The fluorinating agents include AgF$_2$, borontrifluoride etherate and hydrogen fluoride. The reaction is done in an appropriate anhydrous solvent. This reaction gives a mixture of fluorinated cyclodextrins which is purified on an alumina column.

B.3. Reaction of free OH group at C-2

This involves reaction of Per 3,6-anhydro-β-CD (reference 43) with a fluorinating agent either directly or via formation of heptakis (2-halo-3,6-anhydro)-β-CD (reference 44) followed by opening of anhydro linkage by alkaline hydrolysis to yield heptakis 2-(fluoro-2-deoxy)-β-cyclodextrin.

Example 4

Biodistribution Studies

6-F$_3$βCD (90 mg/ml in water) was administered to a BALB/C mouse by intravenous injection through the tail vein, at a dose of 13.5 mg 6-F$_3$βCD per mouse. The mouse was placed in a beaker layered with filter paper to absorb the urine excreted during the experiment. 15 minutes after administration of the drug complex, blood was collected by cardiac puncture, the mouse was sacrificed by euthanasia in dry ice and the desired organs were collected by dissection. All samples were immediately frozen and held frozen until NMR studies.

The biodistribution of 6-F$_3$βCD at 15 minutes after a single intravenous dose is shown in Table 3.

TABLE 3

| Organ | % Dose |
|---|---|
| liver | 4.09 |
| kidney | 1.87 |
| intestine | 0.72 |
| tail | 2.14 |
| blood | 62.59 |
| urine | 40.96 |

After intravenous injection of 6-F$_3$βCD, metabolic degradation over the first fifteen minutes accounts for far less than 5% of the administered dose.

Figure 2:
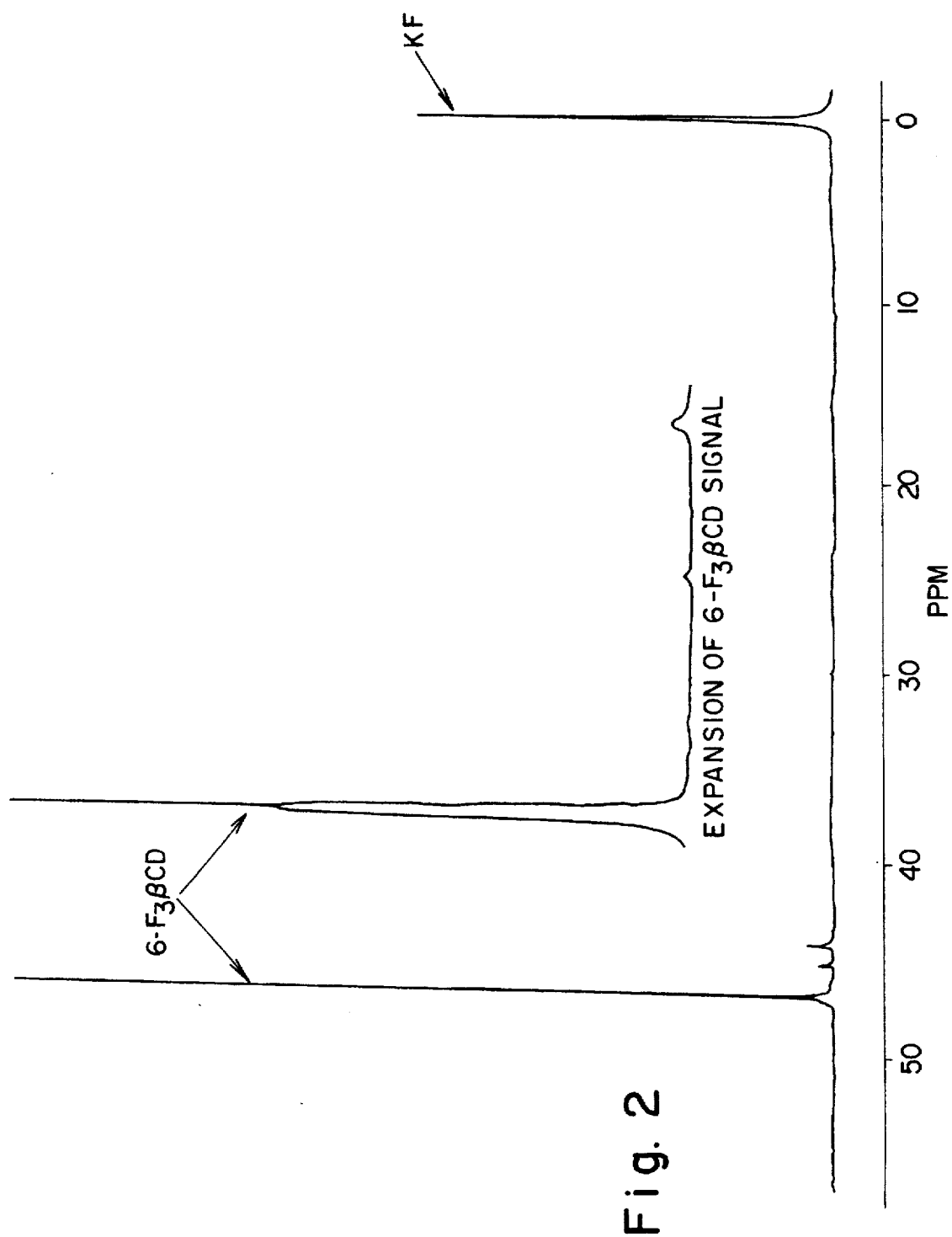
FIG. 2 shows $^{19}$F NMR spectrum of mouse blood after 6-F$_3$βCD administration.
Figure 3:
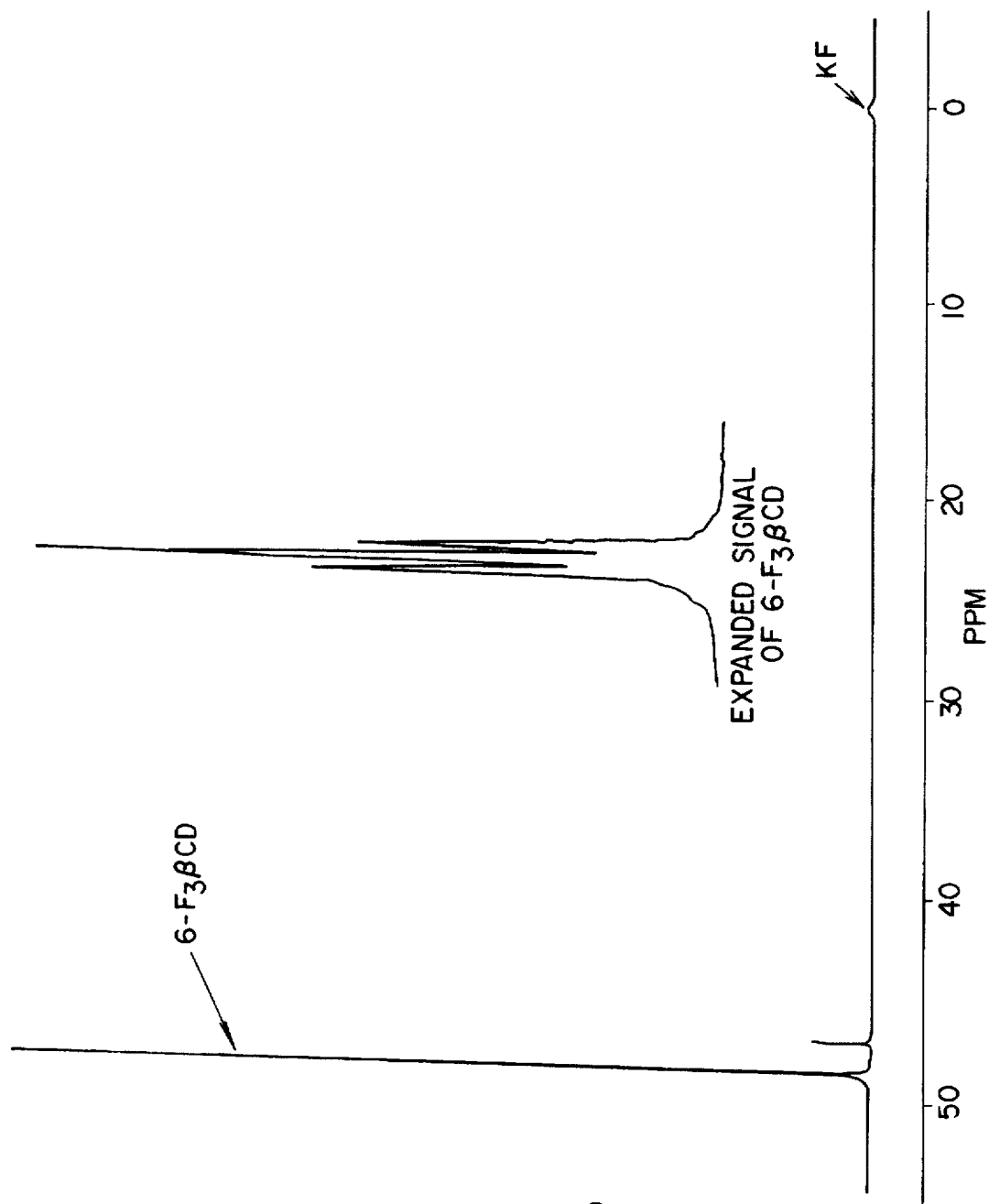
FIG. 3 shows $^{19}$F NMR spectrum of mouse urine after 6-F$_3$βCD administration.

FIGS. 1, 2 and 3 show $^{19}$F NMR spectrum of mouse intact liver, blood and urine respectively at 15 minutes after intravenous administration of 6-F$_3$βCD.

Example 5

6-F$_3$βCD/Flutamide Inclusion Complex

An inclusion complex of 6-F$_3$βCD and flutamide, a non-steroidal fluorine-containing nitrophenyl propamide used for its anti-androgen effects in prostate cancer chemotherapy, was prepared as described in Example 2.

Figure 4:
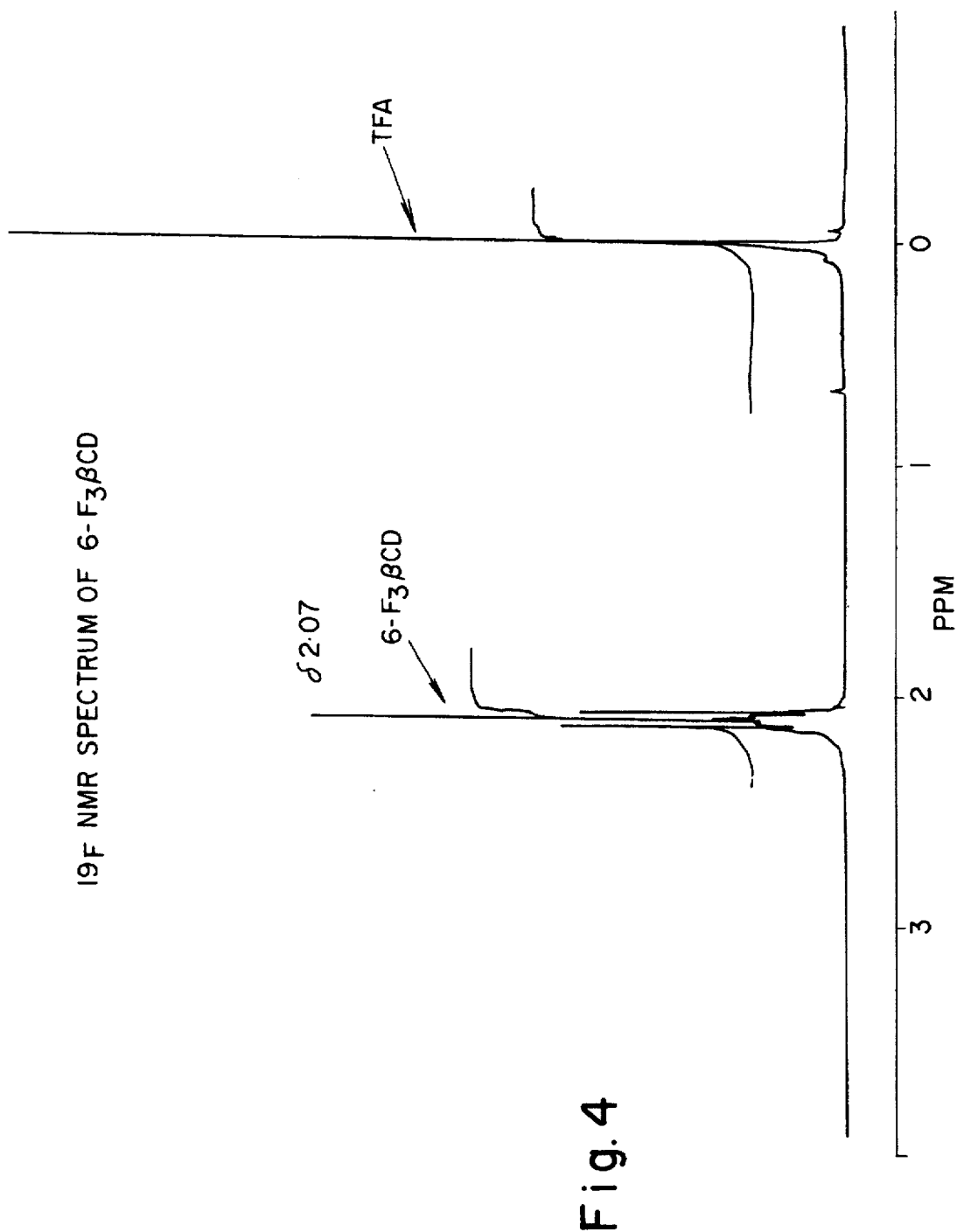
FIG. 4 shows $^{19}$F NMR spectrum of 6-F$_3$βCD.
Figure 5:
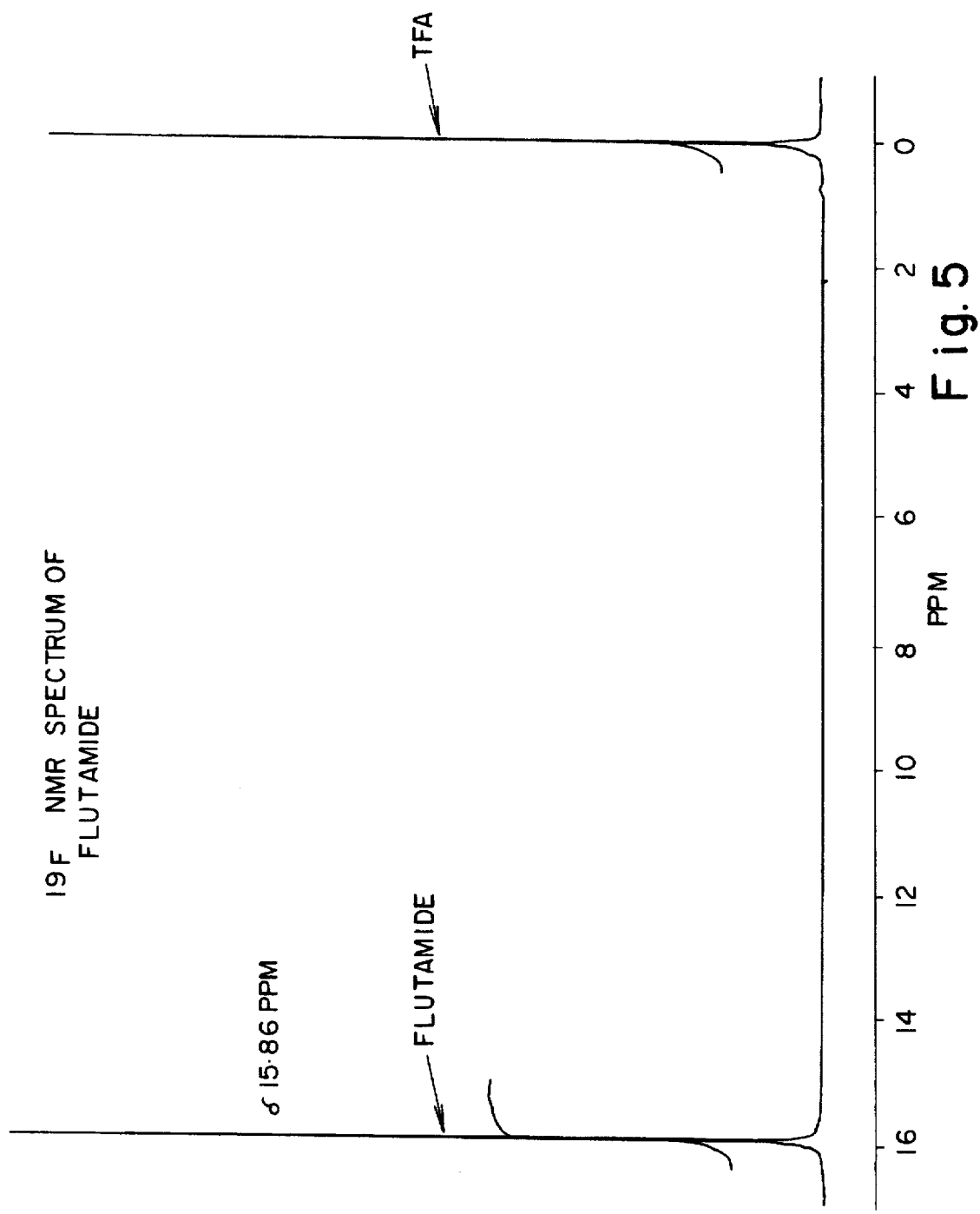
FIG. 5 shows $^{19}$F NMR spectrum of flutamide.
Figure 6:
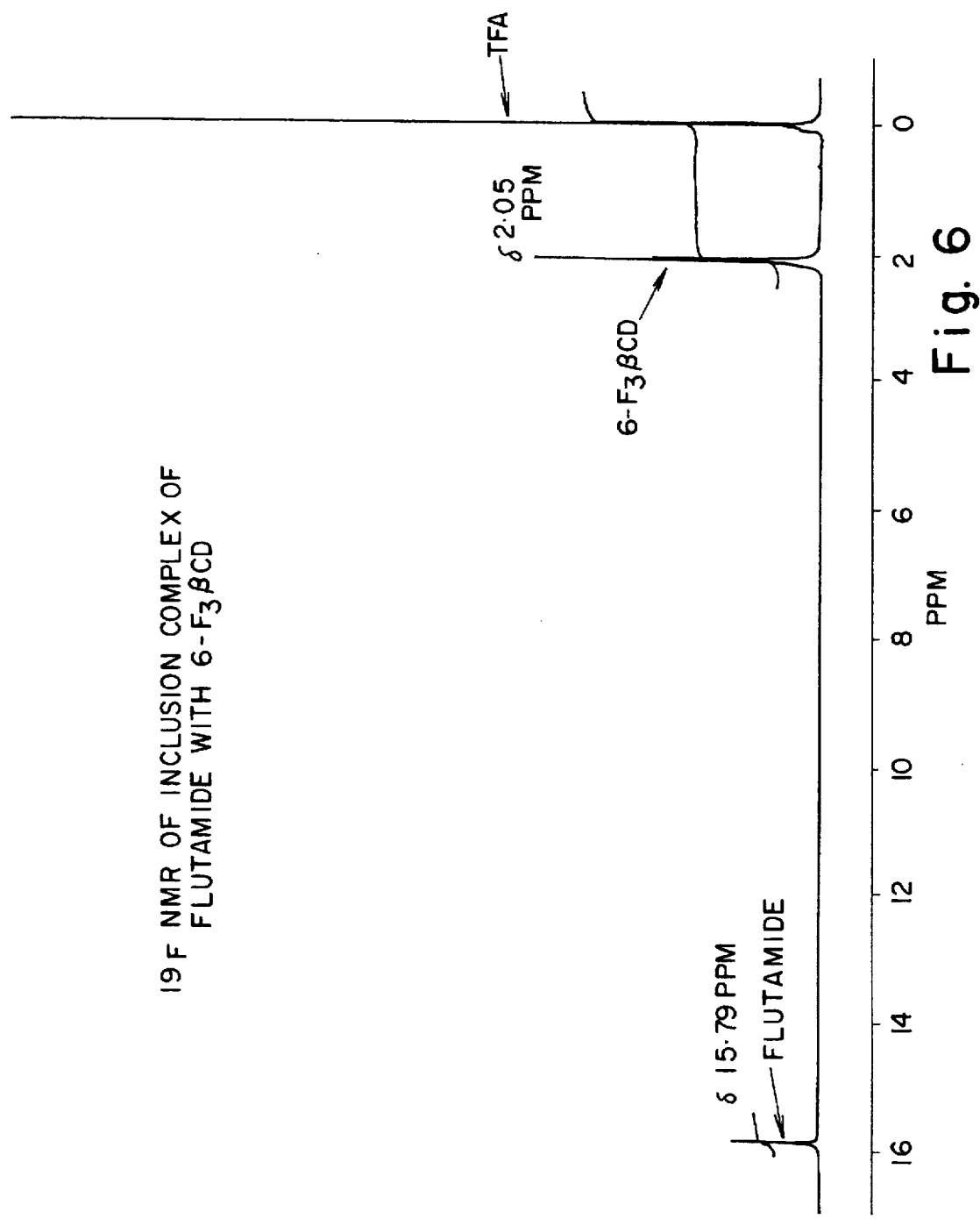
FIG. 6 shows $^{19}$F NMR spectrum of inclusion complex of flutamide with 6-F$_3$βCD.

$^{19}$F MRS studies were performed. The results are shown in FIGS. 4, 5 and 6 and in Table 2.

Example 6

6-F$_3$βCD Flurbiprofen Complex

An inclusion complex of 6-F$_3$βCD and flurbiprofen, a propionic acid-based, fluorine-containing, non-steroidal anti-inflammatory drug, was prepared as described in Example 2.

Figure 7:
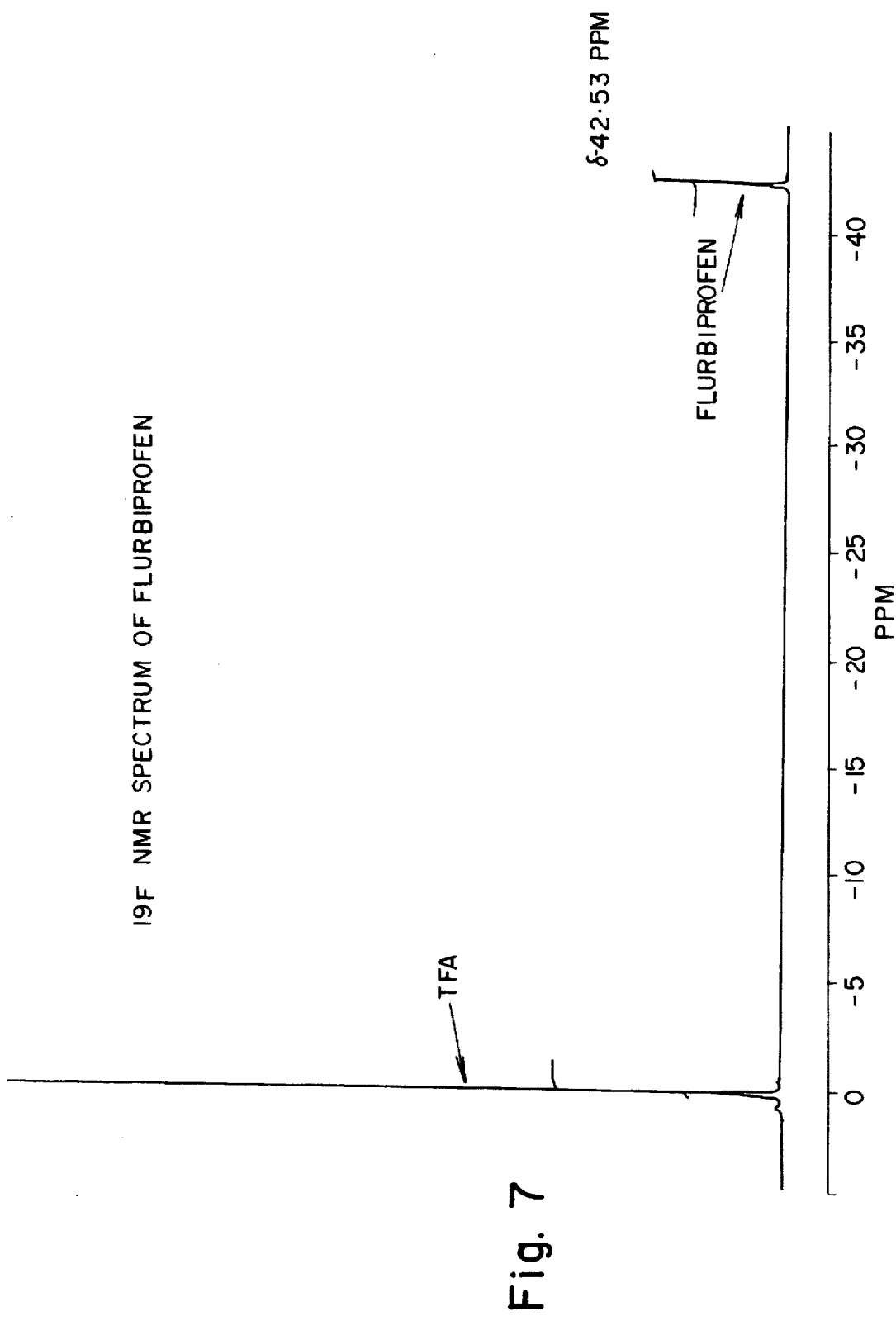
FIG. 7 shows $^{19}$F NMR spectrum of flurbiprofen.
Figure 8:
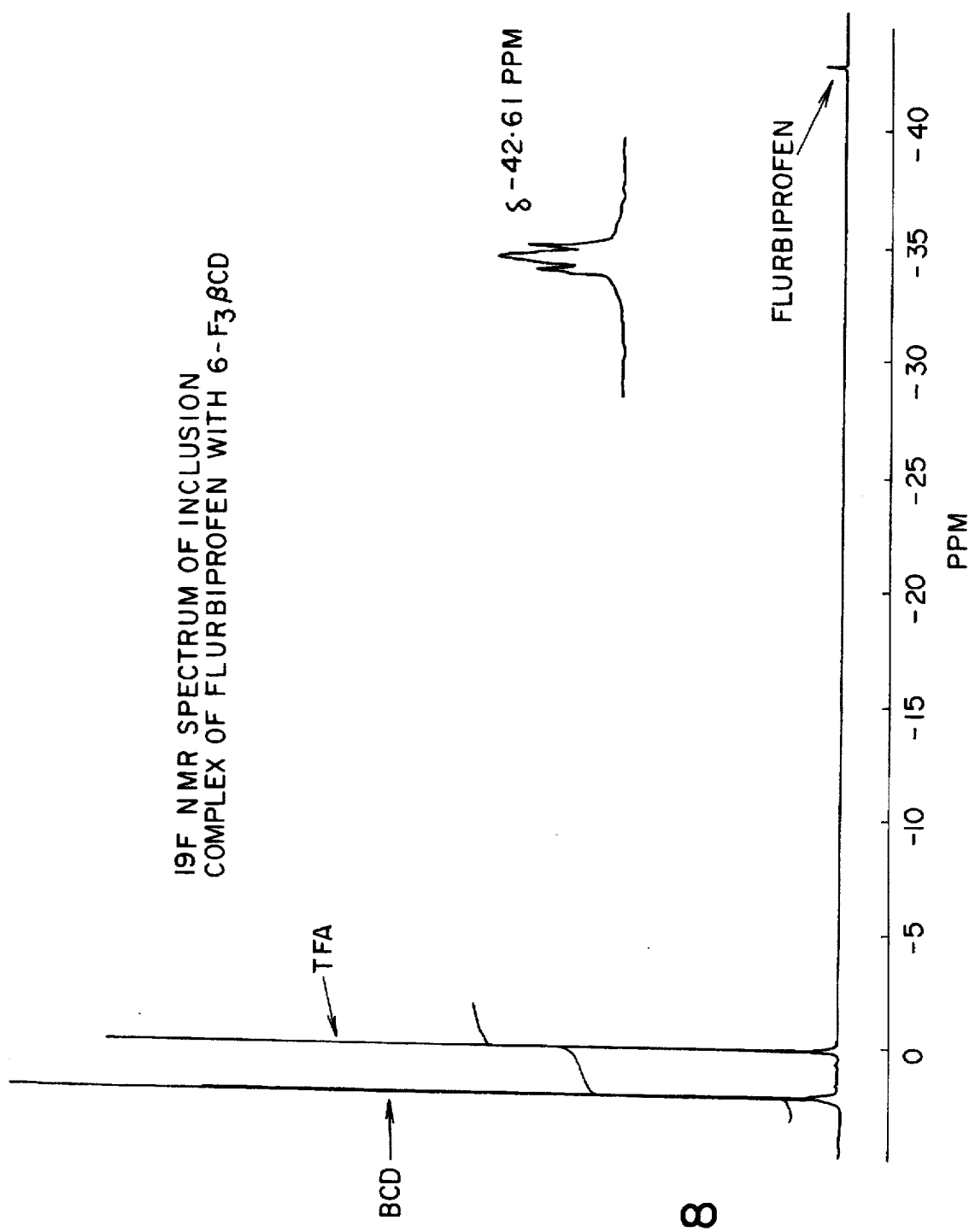
FIG. 8 shows $^{19}$F NMR spectrum of inclusion complex of flurbiprofen with 6-F$_3$βCD.
Figure 9:
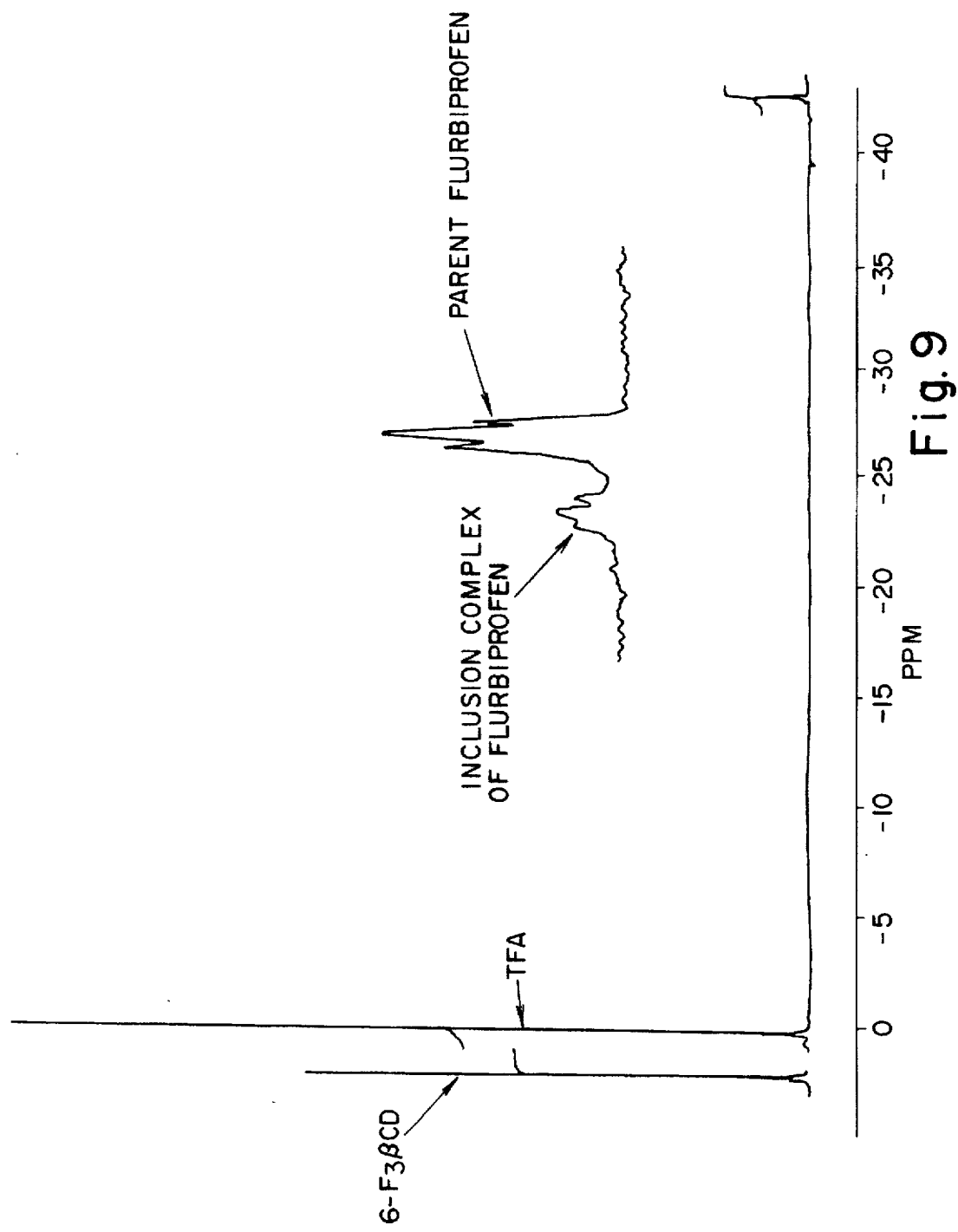
FIG. 9 shows $^{19}$F NMR spectrum of inclusion complex of flurbiprofen with 6-F$_3$βCD plus parent flurbiprofen.
Figure 10:
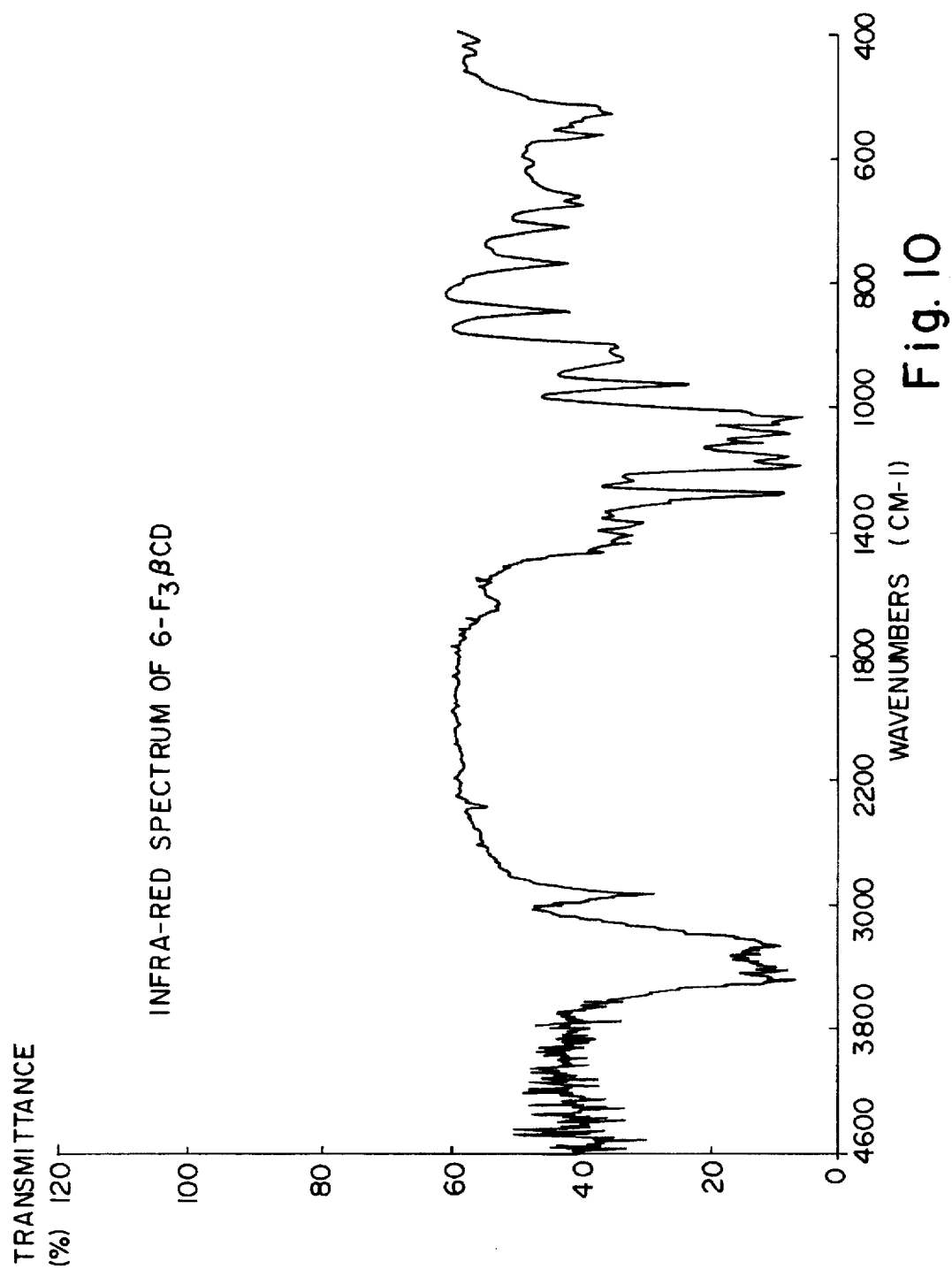
FIG. 10 shows IR spectrum of 6-F$_3$βCD.
Figure 11:
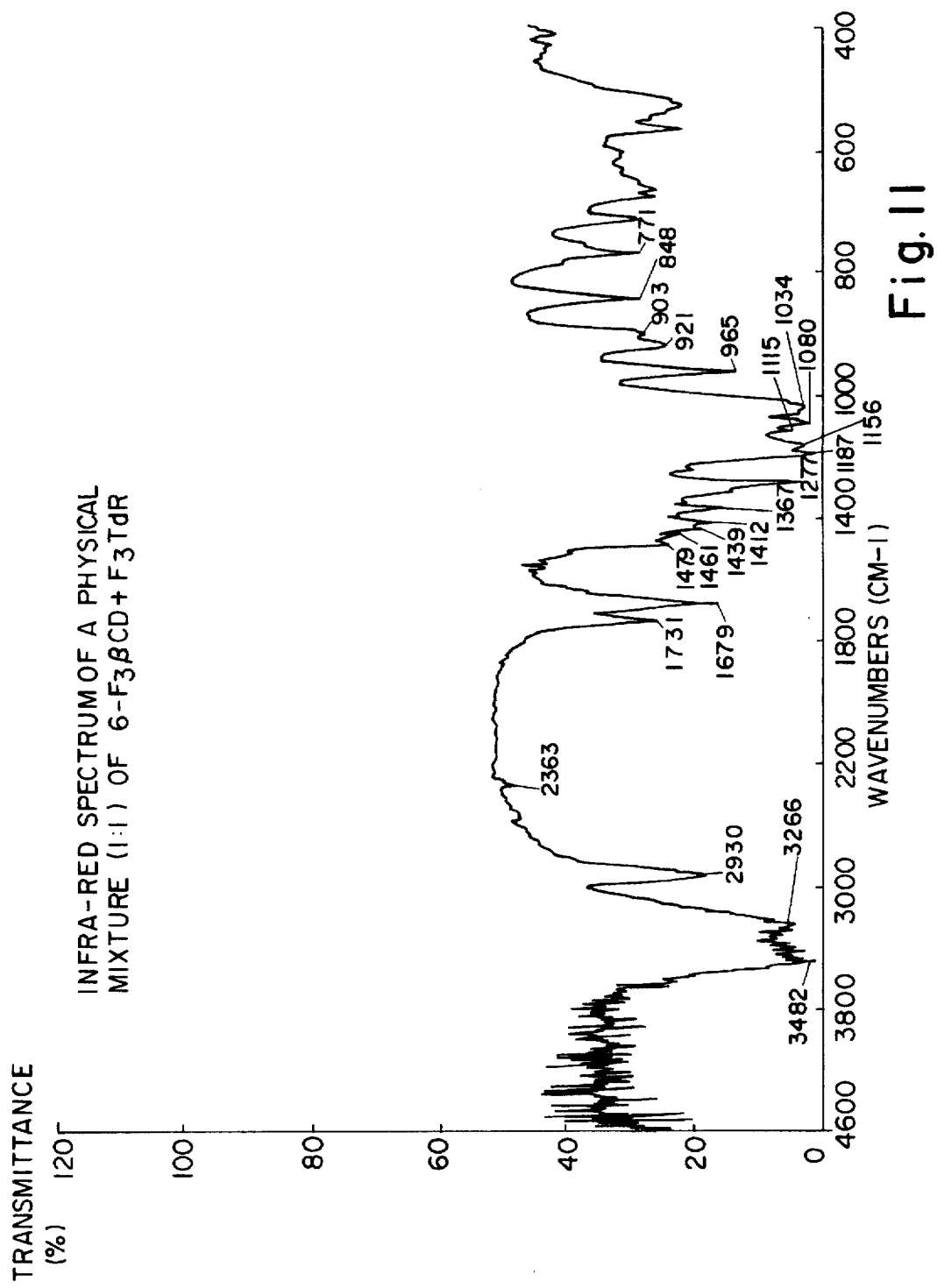
FIG. 11 shows IR spectrum of physical mixture (1:1) of 6-F$_3$βCD and trifluridine.

$^{19}$F MRS studies were performed and the results are shown in FIGS. 7, 8 and 9 and Table 2.

References

1. Naser-Hijazi, B., M. R. Gerger, D. Schmähl, P. Schlag and W. E. Hull. Locoregional Administration of 5-fluoro-2'-deoxyuridine (FdUrd) in Novikoff Hepatoma in the Rat: Effects of Dose and Infusion Time on Tumor Growth and on FdUrd Metabolite Levels in Tumor Tissue as Determined by $^{19}$F-NMR Spectroscopy. *J. Cancer Res. Clin. Oncol.*, 117, 295–304 (1991).

2. Koutcher, J. A., R. C. Sawyer, A. B. Kornblith, R. L. Stolfi, D. S. Martin, M. L. Devitt, D. Cowburn and C. W. Young. In Vivo Monitoring of Changes in 5-Fluorouracil Metabolism Induced by Methotrexate Measured by $^{19}$F-NMR Spectroscopy. *Magnetic Resonance in Med.*, 19, 113–123 (1991).

3. Port, R. E., B. Bachert and W. Semmler. Kinetic Modeling of in vivo-Nuclear Magnetic Resonance Spectroscopy Data: 5-Fluorouracil in Liver and Liver Tumors. *Clin. Pharmacol. Ther.*, 49, 497–505 (1991).

4. McSheehy, P. M. J., M. J. W. Prior and J. R. Griffiths. Prediction of 5-Fluorouracil Cytotoxicity Towards the Walker Carcinosarcoma Using Peak Integrals of Fluoronucleotides Measured by MRS in vivo *Br. J. Cancer*, 60, 303–309 (1989).

5. Zhang, R., S.-J. Soong, T. Liu, S. Barnes and R. B. Diasio, Pharmacokinetics and Tissue Distribution of 2-Fluoro-β-alanine in Rats. Potential Relevance to Toxicity Pattern of 5-Fluorouracil. *Drug Metab. and Disp.*, 20, 113–119 (1992).

6. Maxwell, R. J., T. A. Frenkiel, D. R. Newell, C. Bauer and J. R. Griffiths. $^{19}$F Nuclear Magnetic Resonance Imaging of Drug Distribution in Vivo: The Disposition of an Antifolate Anticancer Drug in Mice. *Magnetic Resonance in Med.*, 17, 189–196 (1991).

7. Thomas, C., C. Counsell, P. Wood and G. E. Adams. Use of Fluorine-19 Nuclear Magnetic Resonance Spectroscopy and Hydralazine for Measuring Dynamic Changes in Blood Perfusion Volume in Tumors in Mice. *J.N.C.I.*, 84, 174–180 (1992).

8. Tandon, M., P. Kumar, G. Wiebe and L. I. Wiebe. Detection of New Metabolites of Trifluridine (F$_3$TdR) Using $^{19}$F NMR Spectroscopy. *Biochem. Pharmacol.*, 44, 2223–2228 (1992).

9. Tandon, M., P. Kumar and L. I. Wiebe. α-Trifluoromethyl-β-ureido-proprionic acid (F$_3$MUPA): a new metabolite of trifluridine (F$_3$TdR). *Nucleosides and Nucleotides.*, 12(8) in press (1993).

10. Tandon, M., P. Kumar and L. I. Wiebe, α-Trifluoromethyl-β-alanyl glycine (F$_3$MBAG): A novel metabolite of trifluorouridine (F$_3$TdR). (submitted).

11. Heidelberger, D., J. Boohar and B. Kampschoer. Fluorinated Pyrimidines XXIV in vivo Metabolism of 5-Trifluoromethyluracil-2-14-C and 5-Trifluoromethyl-2'-deoxyuridine-2-14-C. *Cancer Res.*, 25, 377–381 (1964).

12. Cramer, F. and H. Hettler. Inclusion Compounds of Cyclodextrins. *Naturwissenschaften*, 54, 624–632 (1967).

13. Uekama, K., Pharmaceutical Applications of Methylated Cyclodextrins. *Pharm. Int.*, March, 61–64 (1985); Uekema, K. and Otagiri, M. Cyclodextrins in Drug Cancer Systems. *CRC Crit. Rev. Therap. Drug Cancer Systems*, 3, 1 (1987).

14. Green, A. R. and J. K. Guillory. Heptakis (2,6-di-O-methyl)-β-cyclodextrin Complexation with Antitumor Agent Chlorambucil. *J. Pharm. Sci.*, 78, 427–341 (1989).

15. Brewster, M. E., J. W. Simpkins, M. S. Hora, W. C. Stern and N. Bodor. The Potential Use of Cyclodextrins in Parenteral Formulations. *J. Parenteral Sci. and Tech.*, 43, 231–240 (1989).

16. Pitha, J. et al., Hydroxypropyl-6-cyclodextrin: Preparation and Characterization; Effects on Solubility of Drugs. *Int. J. Pharm.*, 29, 73–82 (1986).

17. Szejtli, J., A. Liptak, I. Jodal, P. Fugedi, P. Nánási .and A. Neszmelyi. Synthesis and $^{13}$C-NMR Spectroscopy of Methylated beta-Cyclodextrins. *Starch/Stärke*, 32, 165–169 (1980).

18. Valsami, G. N. et al. Complexation Studies of Cyclodextrins with Tricyclic Antidepressants Using Ion-selective Electrodes. *Pharm. Res.*, 9, 94–100 (1992).

19. Frijlink, H. W. et al. The Pharmacokinetics of β-cyclodextrin in the Rat. *Pharm. Res.*, 7, 1248–1252 (1990).

20. Frijlink, H. W. et al. The Effect of Cyclodextrins on the Disposition of Intravenously-injected Drugs in the Rat. *Pharm. Res.*, 8, 380–384 (1991).

21. Loftsson, T. and B. J. Olafsdottir. Cyclodextrin-accelerated Degradation of β-lactain Antibiotics in Aqueous Solution. *Int. J. Pharm.*, 67, R5–7 (1991).

22. Irie, T., K. Fukunaga, A. Yoshida, K. Uekama, H. Fales and J. Pitha. Anorphorus Water-soluble Derivatives of Cyclodextrins: 2-Hydroxyethyl, 3-Hydroxypropyl, 2-Hydroxyisobutyl and Carboxamidomethyl Derivatives of β-cyclodextrin. *Pharm. Res.*, 5, 713–719 (1988).

23. Brereton, I. M., T. M. Spotswood, S. F. Lincoln and E. H. Williams. Fluorine-19 Magnetic Resonance Study of the Inclusion of Fluoro-and Difluoro-trans-cinnamates by α-Cyclodextrin. *J. Chem. Soc., Faraday Trans.*, 1, 80, 3147–56 (1984).

24. Lincoln, S. F., A. M. Hounslow, J. H. Coates and B. G. Dodderidge. The Inclusion of Difluorisal by α and β-Cyclodextrins. A $^{19}$F Nuclear Magnetic Resonance and Spectrophotometric Study. *J. Chem. Soc. Faraday Trans.*, 1, 83, 2697–2703 (1987).

25. Pisaniello, D. L., S. F. Lincoln and J. H. Coates. The Inclusion of Haloperidol and Trifluperidol by α- and β-cyclodextrins. *J. Chem. Soc. Faraday Trans.*, 1, 81, 1247–1253 (1985).

26. Smith, N. J., T. M. Spotswood and S. F. Lincoln. The Inclusion of the Enantiomers of N-Trifluoroacetyl-4-fluorophenylalanine and N-Trifluoroacetylphenylalanine by cyclomaltohexose a $^2$H and $^{19}$F-N.M.R. Study. *Carbohydr. Res.*, 192, 9–15 (1989).

27. Brown, S. E., J. H. Coates, S. F. Lincoln, D. R. Coghlan and C. J. Easton. Chiral Molecular Recognition: A $^{19}$F Nuclear Magnetic Resonance Study of the Diastereoisomer Inclusion Complexes formed between Fluorinated Amino Acid Derivative and α-Cyclodextrin in Aqueous Solution. *J. Chem. Soc. Faraday Trans.*, 1, 87,2699–2703 (1991).

28. Card, P. J. Fluorinated Carbohydrates. Use of (diethylamine) sulfur trifluoride in the synthesis of fluorinated sugars. *J. Org. Chem.*, 48, 393–395 (1983).

29. Kumadaki, I. A review in *Yakugaku Zasshi*, 4095 (1969), cited in "Synthetic Procedures in Nucelic Acid Chemistry", Vol. I, ed. by W. W. Zorbach and R. S. Tipson, Pub. Interscience Publishers (1968).

30. Glaudemans, C. P. J. and Fletcher, H. G. Jr. *J. Org. Chem.*, 28, 3004 (1963), cited in "Synthetic Procedures in Nucelic Acid Chemistry", Vol. I, ed. by W. W. Zorbach and R. S. Tipson, Pub. Interscience Publishers (1968).

31. Reist, E. J., Benitez, A., Goodman, L., Baker, B. R. and Lee, W. W. *J. Org. Chem.*, 27, 3274 (1962), cited in "Synthetic Procedures in Nucelic Acid Chemistry", Vol. I, ed. by W. W. Zorbach and R. S. Tipson, Pub. Interscience Publishers (1968).

32. Reichman, U., Watanabe, K. A. and Fox, J. J. A practical synthesis of 2-deoxy-2-fluoro-D-arabinofuranose derivatives. *Carbohydr. Res.*, 42, 233–240 (1975).

33. Grierson, J. R., Link, J. M., Mathis, C. A., Rasey, J. S. and Krohn, K. A. A Radiosynthesis of Fluorine-18 fluoromisonidazole. *J. Nuc. Med.*, 30, (3), 343–350 (1989).

34. Shimada, K., Fukuda, T. T. *Japan Kokai*, 75, 46, 825 (1975) cited in "Cyclodextrins and Their Inclusion Complexes" by J. Szejtli., Publ. Akademiai Kiado, Budapest, p100 (1982).

35. Hoffman, J. L. and R. M. Bock. The Interaction of Cyclodextrins with Nucleic Acids. A Study of Secondary Structure in Three Transfer Ribonucleic Acids. *Biochem.*, 9, 3542–3550 (1970).

36. Taylor, N. F., Childs, R. F. and Brunt, R. V. Synthesis of methyl 3-deoxy-3-fluoro-β-L-xylopyranoside, Chem. Ind. 928 (1964).

37. Breslow, R., Czarnleckl, M. F., Amert, J. and Hamaguchi, H. J. Amer. Chem. Soc., 102, 762 (1980).

38. Tsujihara, K. and Kurita, H., Chem. Lett. 1333 (1978).

39. Cramer, F., Mackensen, G. and Sensse, K., Chem. Ber., 102, 494 (1969).

40. Takeo, K., Suimimoto, T. and Kuge, T., Staerke, 26, 111 (1974).
41. Onozuka, S., Kojima, M., Hattori, K. and Toda, F., Bull. Chem. Soc. Jpn., 53 3221 (1980).
42. Khan, A. R., Barton, L. and D'Souza, V. T., J. Chem. Soc., Chem. Commun. 1112–1114 (1992).
43. Ashton, P. R., Ellwood, P., Staton, I. and Stoddard, J. F., Angew. Chem. Int. Ed. Engl., 30, 80–81 (1991).
44. Gadelle, A. and Defaye, J., Angew. Chem. Int. Ed. Engl., 30, 78–79 (1991).
45. Wenz, Gerhard, "Cyclodextrins as Building Blocks for Supramolecular Structures and Functional Units," *Angewandie Chemie Int. Ed. Engl.* 1994, 33,803–822.
46. Szejtii, "Medicinal Applications of Cyclodextrins," *Medicinal Research Reviews*, Vol. 14, No. 3, 353–386 (1994).

We claim:

1. A cyclic oligosaccharide compound wherein the saccharide monomers are in pyranoside form, said compound comprising at least two fluorine atoms, each attached to said cyclic oligosaccharide or to a substituent such that no greater than three atoms are positioned between said fluorine atom and said cyclic structure.

2. A compound as recited in claim 1, wherein said cyclic oligosaccharide is a cyclodextrin.

3. A compound as recited in claim 2, wherein said cyclodextrin is selected from the group consisting of α-CD, β-CD and γ-CD.

4. A compound as recited in claim 2, selected from the group consisting of:
   heptakis-6-fluoro-6-deoxy-β-cyclodextrin,
   heptakis-3-fluoro-3-deoxy-β-cyclodextrin,
   heptakis-6-fluoro-3-deoxy-β-cycloaltrin,
   6-monotrifluoroethylthio-6-deoxy-β-cyclodextrin, and
   heptakis-trifluoroethyl-β-cyclodextrin.

5. A compound as recited in claim 2, selected from the group consisting of:
   (a) compounds having the formula:

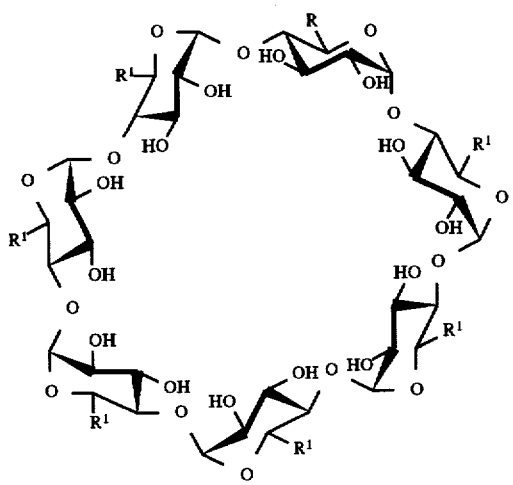

wherein
(i) $R=R^1=F$;
(ii) $R=CH_2F$, one or more $R^1=CH_2OH$, the remaining $R^1=CH_2F$; i.e. for β-CD, $R^1=x$ $CH_2OH$, $(6-x)$ $CH_2F$, $x=0-6$;
(iii) $R=CH_2F$, one or more $R^1=CO_2H$, the remaining $R^1=CH_2F$; i.e. for β-CD, $R^1=x$ $CO_2H$, $(6-x)$ $CH_2F$, $x=0-6$;
(iv) $R=CH_2F$, one or more $R^1=CH_2R^2$ (where $R^2=NH_2$ or $N_3$), the remaining $R^1=CH_2F$; i.e. for β-CD, $R^1=x$ $CH_2R^2$ (where $R^2=NH_2$ or $N_3$), $(6-x)$ $CH_2F$, $x=0-6$;
(v) $R=CH_2F$, one or more $R^1=CH_2OR^2$ (where $R^2$=sugar moiety i.e. Glc, GlcNAc, Gal, GalNAc, Fuc, Neu5Ac, or other suitable sugar moieties), the remaining $R^1=CH_2F$; i.e. for β-CD, $R^1=x$ $CH_2OR^2$ (where $R^2$=sugar moiety i.e. Glc, GlcNAc, Gal, GalNAc, Fuc, Neu5Ac, or other suitable sugar moieties), $(6-x)$ $CH_2F$, $x=0-6$;
(vi) R is $CH_2OCH_2CF_3$, or $CH_2NHC_6H_4F$, or other moieties which contain fluorine, each $R^1$ each $R^1$ equals F, $CH_2OH$, $CH_2F$, $CH_2R^2$ or $CH_2OR^2$ (where $R^2$ is as defined above);

(b) compounds having the formula:

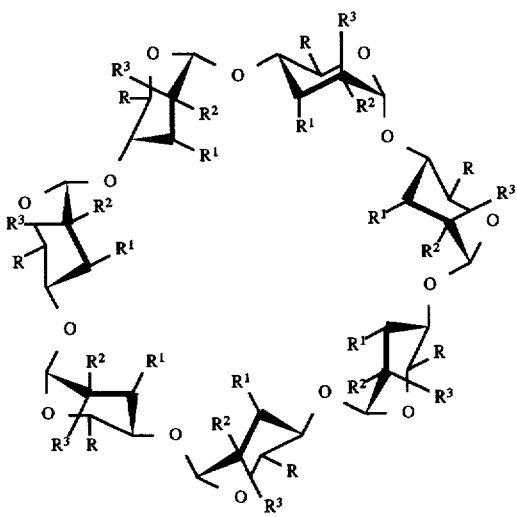

wherein:
(i) $R=CH_2OH$, $R^1=F$, $R^2=OH$, $R^3=H$;
(ii) $R^1=F$, $R^2=OH$, $R^3=H$, at least one $R=CO_2H$, the remaining $R=CH_2OH$; i.e. for β-CD, $R=x$ $CO_2H$, $(7-x)$ $CH_2OH$, $x=0-7$;
(iii) $R^1=F$, $R^2=OH$, $R^3=H$, at least one $R=CH_2R^4$ (where $R^4=NH_2$ or $N_3$), the remaining $R=CH_2OH$, i.e. for β-CD, $R=x$ $CH_2R^4$ (where $R^4=NH_2$ or $N_3$), $(7-x)$ $CH_2OH$, $x=0-7$;
(iv) $R^1=F$, $R^2=OH$, $R^3=H$, at least one $R=CH_2R^5$ (where $R^5$=sugar moiety i.e. Glc, GlcNAc, Gal, GalNAc, Fuc, Neu5Ac, or other suitable sugar moieties), the remaining $R=CH_2OH$; i.e. for β-CD, $R=x$ $CH_2R^5$ (where $R^5$=sugar moiety i.e. Glc, GlcNAc, Gal, GalNAc, Fuc, Neu5Ac, or other suitable sugar moieties), $(7-x)$ $CH_2OH$, $x=0-7$;
(v) $R=CH_2OH$, $R^1=F$, $R^2=H$, $R^3=OH$;
(vi) $R^1=F$, $R^2=H$, $R^3=OH$, at least one $R=CO_2H$, the remaining $R=CH_2OH$; i.e. for β-CD, $R=x$ $CO_2H$, $(7-x)$ $CH_2OH$, $x=0-7$;
(vii) $R^1=F$, $R^2=H$, $R^3=OH$, at least one $R=CH_2R^4$ (where $R^4=NH_2$ or $N_3$), the remaining $R=CH_2OH$; i.e. for β-CD, $R=x$ $CH_2R^4$ (where $R^4=NH_2$ or $N_3$), $(7-x)$ $CH_2OH$, $x=0-7$;
(viii) $R^1=F$, $R^2=H$, $R^3=OH$, at least one $R=CH_2OR^5$ (where $R^5$=sugar moiety i.e. Glc, GlcNAc, Gal, GalNAc, Fuc, Neu5Ac, or other suitable sugar moieties), the remaining $R=CH_2OH$; i.e. for β-CD, $R=x$ $CH_2OR^5$ (where $R^5$=sugar moiety i.e. Glc, GlcNAc, Gal, GalNAc, Fuc, Neu5Ac, or other suitable sugar moieties), (7−x) CH$_2$OH, x=0−7;

(c) compounds having the formula:

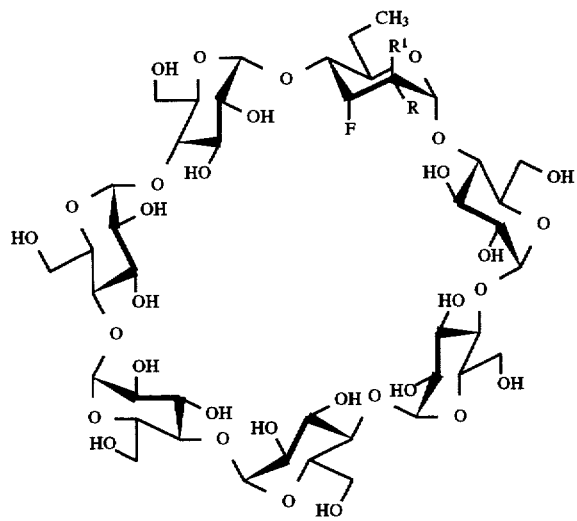

wherein:

(i) R=OH, R$^1$=H;
(ii) R=H, R$^1$=OH.

6. A complex comprising a fluorine-containing cyclic oligosaccharide as recited in claim 1 and a drug.

7. A complex as recited in claim 6, wherein said drug is selected from the group consisting of mitoxantrone, taxol, progesterone, testosterone, ibuprofen, hydrocortisone, digitoxin, digoxin, diazepam, and peptides, fluorinated analogs of mitoxantrone, taxol, progesterone, testosterone, ibuprofen, hydrocortisone, digitoxin, digoxin, diazepam, and peptides, fluorinated amino acids and peptides, F$_3$TDR, fluorouracil and fluorinated pyridoxyl analogs.

8. A complex as recited in claim 6, wherein said cyclic oligosaccharide is a cyclodextrin.

9. A pharmaceutical composition comprising complex as recited in claim 6 together with a suitable complex carrier or excipient.

10. A process of making a fluorine-containing oligosaccharide compound of claim 1 wherein the saccharide monomers are in pyranoside form, comprising reacting a fluorine containing compound with a cyclic oligosaccharide to form said fluorine-containing oligosaccharide compound, said fluorine atom thereby becoming attached to said cyclic oligosaccharide or to a substituent such that no greater than three atoms are positions between said fluorine atom and said cyclic oligosaccharide.

11. A process as recited in claim 10, wherein said cyclic oligosaccharide is a cyclodextrin.

12. A process as recited in claim 10, wherein said process comprises at least one process step selected from the group consisting of:

(1)

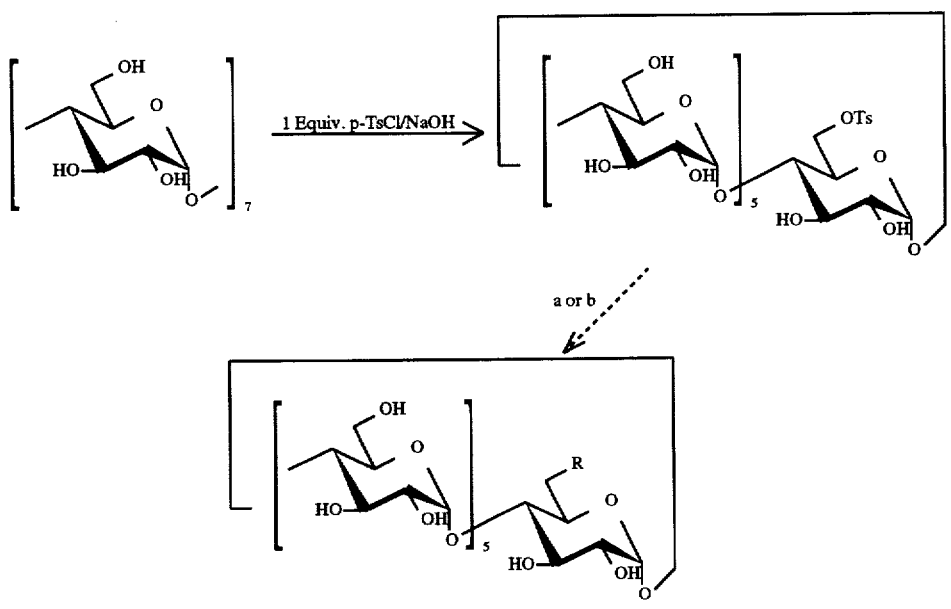

Synthesis of 6-Fluoro-β-CD
(2)
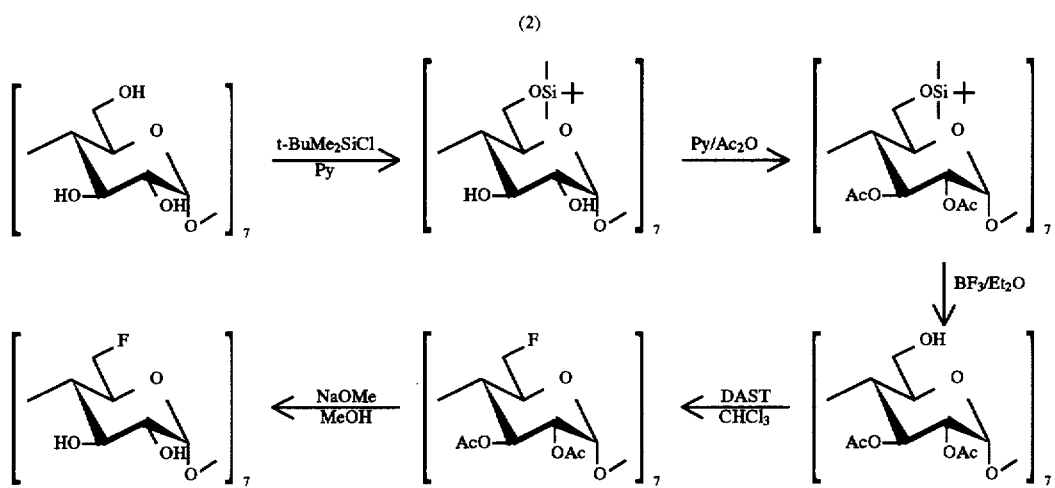
Synthesis of 3-Fluoro-β-CD
(3)
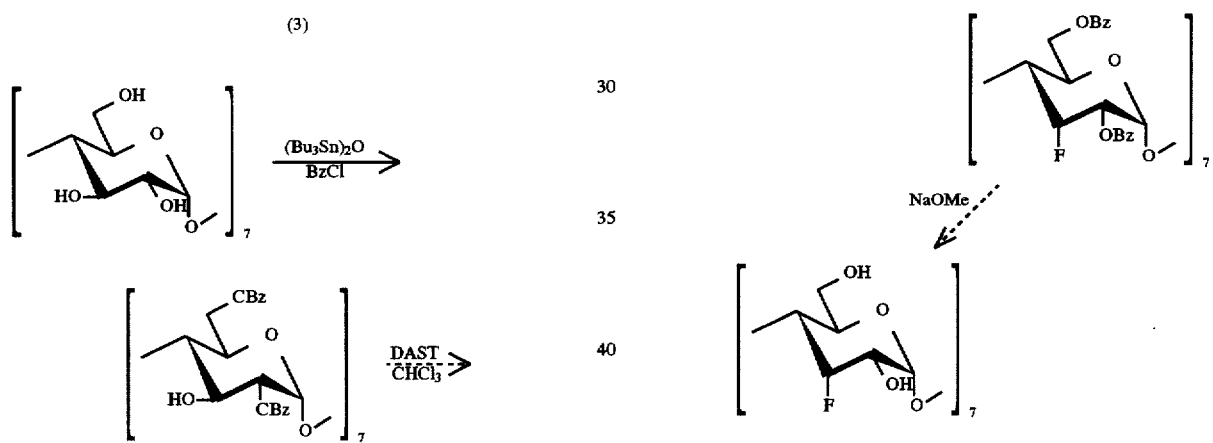
-continued
Synthesis of 3-Fluoro-β-CD
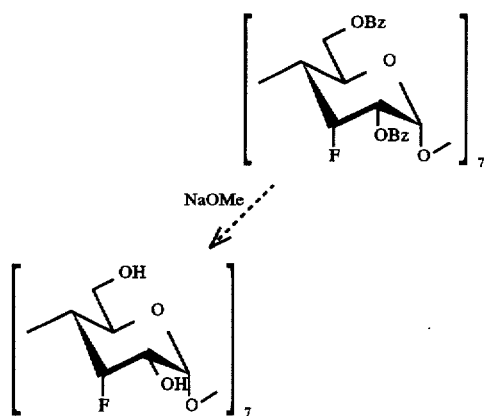
Synthesis of 3-Fluoro-Manno-β-CD
(4)
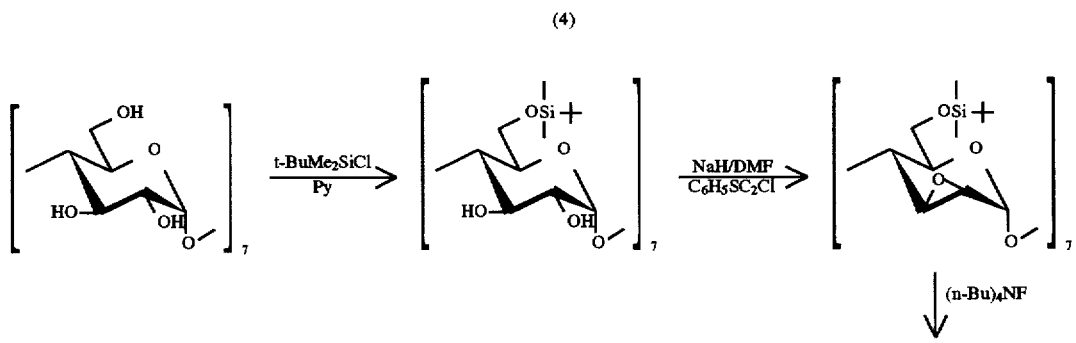

-continued
Synthesis of 3-Fluoro-Manno-β-CD

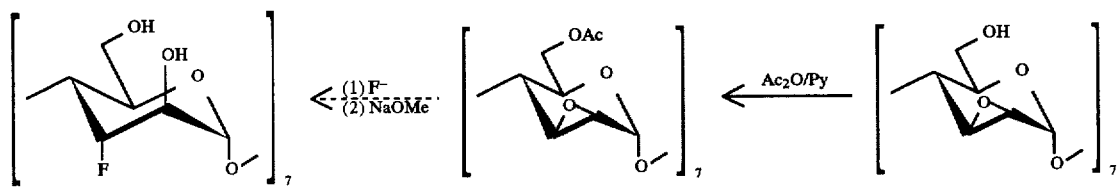

(5) reacting β-CD with 2,2,2-trifluoroethanol;
(6) reacting β-CD with diethylaminosulfur trifluoride;
(7) reacting β-CD with antimony pentafluoride;
(8) reacting cyclodextrin with hydrogen fluoride;
(9) reacting cyclodextrin with a metal fluoride selected from the group consisting of AgF, AgF$_2$ and KF;
(10) reacting cyclodextrin with BF$_3$ etherate.

13. A process for making a complex comprising a fluorine-containing cyclic oligosaccharide as recited in claim 1 and a drug, the process comprising mixing a fluorine-containing oligosaccharide as recited in claim 1 with a drug.

14. A process as recited in claim 13, wherein said cyclic oligosaccharide is a cyclodextrin.

15. A process for providing site specific delivery of a drug to a patient, comprising administering to a patient in need of treatment with said drug a complex as recited in claim 6.

16. A process as recited in claim 15, wherein said cyclic oligosaccharide is a cyclodextrin.

17. A process for analyzing in vivo the location and time of drug release from a complex as recited in claim 6, said process comprising administering said complex to a patient and performing $^{19}$F MRS on said patient.

18. A process for analyzing in vivo activity of a drug, said process comprising administering to a patient a complex as recited in claim 6, and performing $^{19}$F MRS on said patient.

19. A method for determining the location of tumor in a patient using $^{19}$F MRI comprising administering a complex as recited in claim 6.

20. A method of analyzing tissue extracted from a living being comprising treating said tissue with a complex as recited in claim 6 and subsequently analyzing said tissue using $^{19}$F MRS.

21. A complex comprising the cyclic oligosaccharide compound of claim 1 and at least one additional compound selected from the group consisting of an amino acid, a peptide and a carbohydrate antigen.

22. A complex comprising a fluorine-containing cyclic oligosaccharide compound as recited in claim 2 and a drug.

23. A complex comprising a fluorine-containing cyclic oligosaccharide compound as recited in claim 3 and a drug.

24. A complex comprising a fluorine-containing cyclic oligosaccharide compound as recited in claim 4 and a drug.

25. A complex comprising a fluorine-containing cyclic oligosaccharide compound as recited in claim 5 and a drug.

* * * * *